(12) United States Patent
Tuseth

(10) Patent No.: US 11,110,266 B2
(45) Date of Patent: Sep. 7, 2021

(54) TRANSCATHETER SYSTEM AND METHOD FOR REGULATING FLOW OF FLUID BETWEEN TWO ANATOMICAL COMPARTMENTS

(71) Applicant: NUHEART AS, Bergen (NO)

(72) Inventor: Vegard Tuseth, Bergen (NO)

(73) Assignee: NUHEARI AS, Bergen (NO)

( * ) Notice: Subject to any disclaimer, the term of this patent is extended or adjusted under 35 U.S.C. 154(b) by 36 days.

(21) Appl. No.: 16/134,626

(22) Filed: Sep. 18, 2018

(65) Prior Publication Data

US 2019/0015568 A1    Jan. 17, 2019

Related U.S. Application Data

(63) Continuation of application No. 15/112,401, filed as application No. PCT/EP2015/055578 on Mar. 17, 2015, now Pat. No. 10,130,742.

(30) Foreign Application Priority Data

Mar. 17, 2014 (NO) ............................... NO20140353
Jun. 10, 2014 (GB) ..................................... 1410320

(51) Int. Cl.
*A61M 1/10* (2006.01)
*A61M 60/857* (2021.01)
(Continued)

(52) U.S. Cl.
CPC ..... *A61M 60/857* (2021.01); *A61B 17/00234* (2013.01); *A61B 17/11* (2013.01);
(Continued)

(58) Field of Classification Search
CPC ........ A61M 1/12; A61M 1/125; A61M 1/122; A61M 1/1008; A61M 1/10; A61M 2205/04; A61M 2205/10–2205/103; A61M 2205/33; A61M 2205/3368; A61M 2206/20; A61M 2210/12–2210/127; A61B 17/00234; A61B 2017/00252; A61B 2017/00867; A61B 2017/00876;
(Continued)

(56) References Cited

U.S. PATENT DOCUMENTS 3,997,923 A * 12/1976 Possis .................. A61F 2/2409
                                                        623/2.4
5,571,215 A    11/1996 Sterman et al.
(Continued)

FOREIGN PATENT DOCUMENTS

AU    2014201432 A1    10/2014
EP       1907028 A1     4/2008
(Continued)

*Primary Examiner* — Paul B Prebilic
(74) *Attorney, Agent, or Firm* — BakerHostetler

(57) ABSTRACT

The present invention relates to a transcatheter method for providing fluid communication between two anatomical compartments. The present invention also relates to a transcatheter system comprising an intracorporeal connector for fluid communication between two anatomical compartments through at least one anatomical wall, wherein said connector is adapted to receive a flow regulating device, a connector, a flow regulating device and an insertion device.

17 Claims, 32 Drawing Sheets

(51) Int. Cl.

| | | |
|---|---|---|
| *A61B 17/34* | (2006.01) | |
| *A61M 29/00* | (2006.01) | |
| *A61M 60/00* | (2021.01) | |
| *A61M 60/40* | (2021.01) | |
| *A61M 60/50* | (2021.01) | |
| *A61M 60/135* | (2021.01) | |
| *A61M 60/148* | (2021.01) | |
| *A61M 60/205* | (2021.01) | |
| *A61B 17/11* | (2006.01) | |
| *A61M 27/00* | (2006.01) | |
| *A61B 17/00* | (2006.01) | |
| *A61M 25/06* | (2006.01) | |
| *A61M 25/04* | (2006.01) | |
| *A61M 60/871* | (2021.01) | |
| *A61M 25/09* | (2006.01) | |

(52) U.S. Cl.
CPC ...... *A61B 17/3468* (2013.01); *A61B 17/3478* (2013.01); *A61B 27/002* (2013.01); *A61M 29/00* (2013.01); *A61M 60/00* (2021.01); *A61M 60/135* (2021.01); *A61M 60/148* (2021.01); *A61M 60/205* (2021.01); *A61M 60/40* (2021.01); *A61M 60/50* (2021.01); *A61B 2017/00243* (2013.01); *A61B 2017/00247* (2013.01); *A61B 2017/00252* (2013.01); *A61B 2017/00685* (2013.01); *A61B 2017/00867* (2013.01); *A61B 2017/00876* (2013.01); *A61B 2017/1107* (2013.01); *A61B 2017/1139* (2013.01); *A61B 2017/3488* (2013.01); *A61M 25/04* (2013.01); *A61M 25/0662* (2013.01); *A61M 25/09* (2013.01); *A61M 27/006* (2013.01); *A61M 60/871* (2021.01); *A61M 2025/0681* (2013.01); *A61M 2205/8243* (2013.01)

(58) Field of Classification Search
CPC ........ A61B 17/3439; A61B 2560/0406; A61B 2560/0443; A61B 2560/045; A61B 2560/0456
See application file for complete search history.

(56) References Cited

U.S. PATENT DOCUMENTS

| | | | |
|---|---|---|---|
| 5,728,122 A | 3/1998 | Leschinsky et al. | |
| 5,921,913 A | 7/1999 | Siess | |
| 6,134,467 A | 10/2000 | Ouchi | |
| 6,196,230 B1 | 3/2001 | Hall et al. | |
| 6,425,916 B1 | 7/2002 | Garrison et al. | |
| 7,295,878 B1 | 11/2007 | Meadows et al. | |
| 7,878,967 B1 | 2/2011 | Khanal | |
| 7,942,804 B2 * | 5/2011 | Khaw ................ | F04D 29/247 600/16 |
| 8,157,852 B2 | 4/2012 | Bloom et al. | |
| 8,738,147 B2 | 5/2014 | Hastings et al. | |
| 9,314,556 B2 | 4/2016 | Tuseth | |
| 9,539,378 B2 | 1/2017 | Tuseth | |
| 2001/0047150 A1 | 11/2001 | Chobotov | |
| 2002/0082584 A1 | 6/2002 | Rosenman et al. | |
| 2002/0099396 A1 | 7/2002 | Slaker et al. | |
| 2002/0173742 A1 | 11/2002 | Keren et al. | |
| 2002/0173817 A1 | 11/2002 | Kletschka et al. | |
| 2003/0100920 A1 | 5/2003 | Akin et al. | |
| 2003/0181843 A1 | 9/2003 | Bibber et al. | |
| 2003/0233143 A1 | 12/2003 | Gharib et al. | |
| 2004/0006305 A1 | 1/2004 | Hebert et al. | |
| 2004/0092858 A1 | 5/2004 | Wilson et al. | |
| 2004/0097973 A1 | 5/2004 | Loshakove et al. | |
| 2004/0098081 A1 | 5/2004 | Landreville et al. | |
| 2004/0236170 A1 | 11/2004 | Kim | |
| 2004/0243051 A1 | 12/2004 | Monzyk et al. | |
| 2005/0075696 A1 | 4/2005 | Forsberg et al. | |
| 2005/0165344 A1 | 7/2005 | Dobak | |
| 2005/0187425 A1 | 8/2005 | Alferness et al. | |
| 2006/0079736 A1 | 4/2006 | Chin et al. | |
| 2006/0089707 A1 | 4/2006 | Vassiliades et al. | |
| 2006/0155158 A1 | 7/2006 | Aboul-Hosn | |
| 2007/0249985 A1 | 10/2007 | Brenneman et al. | |
| 2008/0195226 A1 | 8/2008 | Williams et al. | |
| 2008/0269641 A1 | 10/2008 | OShaughnessy et al. | |
| 2008/0300574 A1 | 12/2008 | Belson et al. | |
| 2009/0088597 A1 | 4/2009 | Frazier et al. | |
| 2009/0093670 A1 | 4/2009 | Annest et al. | |
| 2009/0093751 A1 | 4/2009 | Tao et al. | |
| 2009/0105654 A1 | 4/2009 | Kurth et al. | |
| 2009/0182188 A1 | 7/2009 | Marseille et al. | |
| 2009/0228078 A1 | 9/2009 | Zhang et al. | |
| 2010/0191035 A1 | 7/2010 | Kang et al. | |
| 2010/0268316 A1 | 10/2010 | Brenneman et al. | |
| 2010/0331972 A1 | 12/2010 | Pintor et al. | |
| 2011/0130619 A1 | 6/2011 | Whisenant et al. | |
| 2011/0184224 A1 * | 7/2011 | Garrigue ................ | A61M 1/125 600/16 |
| 2011/0196190 A1 | 8/2011 | Farnan et al. | |
| 2011/0234155 A1 | 9/2011 | Chen et al. | |
| 2011/0257723 A1 | 10/2011 | McNamara | |
| 2011/0276075 A1 | 11/2011 | Fung et al. | |
| 2011/0306916 A1 | 12/2011 | Nitzan et al. | |
| 2012/0053657 A1 | 3/2012 | Parker et al. | |
| 2012/0059459 A1 | 3/2012 | Asirvatham et al. | |
| 2012/0139355 A1 | 6/2012 | Ganem et al. | |
| 2012/0146575 A1 | 6/2012 | Armstrong et al. | |
| 2012/0150259 A1 | 6/2012 | Meskens | |
| 2012/0165928 A1 | 6/2012 | Nitzan et al. | |
| 2012/0172654 A1 | 7/2012 | Bates | |
| 2012/0172655 A1 | 7/2012 | Campbell et al. | |
| 2012/0178985 A1 | 7/2012 | Walters et al. | |
| 2012/0232316 A1 | 9/2012 | Nappa | |
| 2012/0245649 A1 | 9/2012 | Bohori et al. | |
| 2012/0259263 A1 | 10/2012 | Celermajer et al. | |
| 2012/0265003 A1 | 10/2012 | DAmbrosio et al. | |
| 2012/0301318 A1 | 11/2012 | Er | |
| 2013/0060267 A1 | 3/2013 | Farnan et al. | |
| 2013/0079872 A1 | 3/2013 | Gallagher | |
| 2013/0127253 A1 | 5/2013 | Stark et al. | |
| 2013/0193914 A1 | 8/2013 | Gaddam et al. | |
| 2013/0301318 A1 | 11/2013 | Asako et al. | |
| 2014/0005466 A1 | 1/2014 | Crosby et al. | |
| 2014/0005768 A1 | 1/2014 | Thomas et al. | |
| 2014/0031607 A1 | 1/2014 | Zilbershlag et al. | |
| 2014/0236123 A1 | 8/2014 | Birmingham et al. | |
| 2014/0287274 A1 | 9/2014 | Hwang | |
| 2014/0336445 A1 | 11/2014 | Farnan et al. | |
| 2015/0005570 A1 | 1/2015 | Fritz et al. | |
| 2015/0119633 A1 | 4/2015 | Haselby et al. | |
| 2015/0223839 A1 | 8/2015 | Spence et al. | |
| 2015/0250935 A1 | 9/2015 | Anderson et al. | |
| 2015/0258260 A1 | 9/2015 | Tuseth | |
| 2015/0258312 A1 | 9/2015 | Tuseth | |
| 2015/0335801 A1 | 11/2015 | Farnan et al. | |
| 2015/0374483 A1 | 12/2015 | Janardhan et al. | |
| 2016/0022896 A1 | 1/2016 | Burkhoff | |
| 2016/0175501 A1 | 6/2016 | Schuermann | |
| 2017/0000935 A1 | 1/2017 | Vasilyev et al. | |
| 2017/0043077 A1 | 2/2017 | Tuseth et al. | |
| 2017/0047762 A1 | 2/2017 | Tuseth et al. | |
| 2017/0106176 A1 | 4/2017 | Taft et al. | |
| 2017/0189063 A1 | 7/2017 | Tuseth et al. | |
| 2017/0189650 A1 | 7/2017 | Tuseth et al. | |
| 2017/0196565 A1 | 7/2017 | Tuseth et al. | |
| 2017/0197019 A1 | 7/2017 | Tuseth et al. | |
| 2017/0216029 A1 | 8/2017 | Crowley et al. | |
| 2018/0098847 A1 | 4/2018 | Tuseth et al. | |

FOREIGN PATENT DOCUMENTS

| | | |
|---|---|---|
| EP | 2338540 A1 | 6/2011 |
| GB | 2504176 A | 1/2014 |
| JP | 2008545083 A | 12/2008 |

(56) References Cited

FOREIGN PATENT DOCUMENTS

| | | |
|---|---:|---:|
| JP | 2012523894 A | 10/2012 |
| WO | WO1997027898 | 8/1997 |
| WO | 0027312 A1 | 5/2000 |
| WO | 2000027312 | 5/2000 |
| WO | 2001078580 | 10/2001 |
| WO | WO2001078580 | 10/2001 |
| WO | 2005037345 A2 | 4/2005 |
| WO | 2007003351 A1 | 1/2007 |
| WO | 2008027869 A2 | 3/2008 |
| WO | WO2008027869 A2 | 3/2008 |
| WO | 2008055301 A1 | 5/2008 |
| WO | WO2008055301 A1 | 5/2008 |
| WO | 2008106717 A1 | 9/2008 |
| WO | WO2008106717 A1 | 9/2008 |
| WO | 2008134267 A2 | 11/2008 |
| WO | WO2008134267 A2 | 11/2008 |
| WO | 2009134471 A1 | 11/2009 |
| WO | WO2009134471 A1 | 11/2009 |
| WO | 2010042056 A1 | 4/2010 |
| WO | WO2010042056 A1 | 4/2010 |
| WO | 2010114666 A1 | 10/2010 |
| WO | 2010121076 A3 | 10/2010 |
| WO | WO2010114666 A1 | 10/2010 |
| WO | 2010132451 A2 | 11/2010 |
| WO | 2011011787 A2 | 1/2011 |
| WO | WO2011011787 A2 | 1/2011 |
| WO | 199727898 | 10/2012 |
| WO | 2013036588 A1 | 3/2013 |
| WO | 2013096965 A1 | 6/2013 |
| WO | 2015075576 A1 | 5/2015 |
| WO | WO2015140179 A2 | 9/2015 |

* cited by examiner

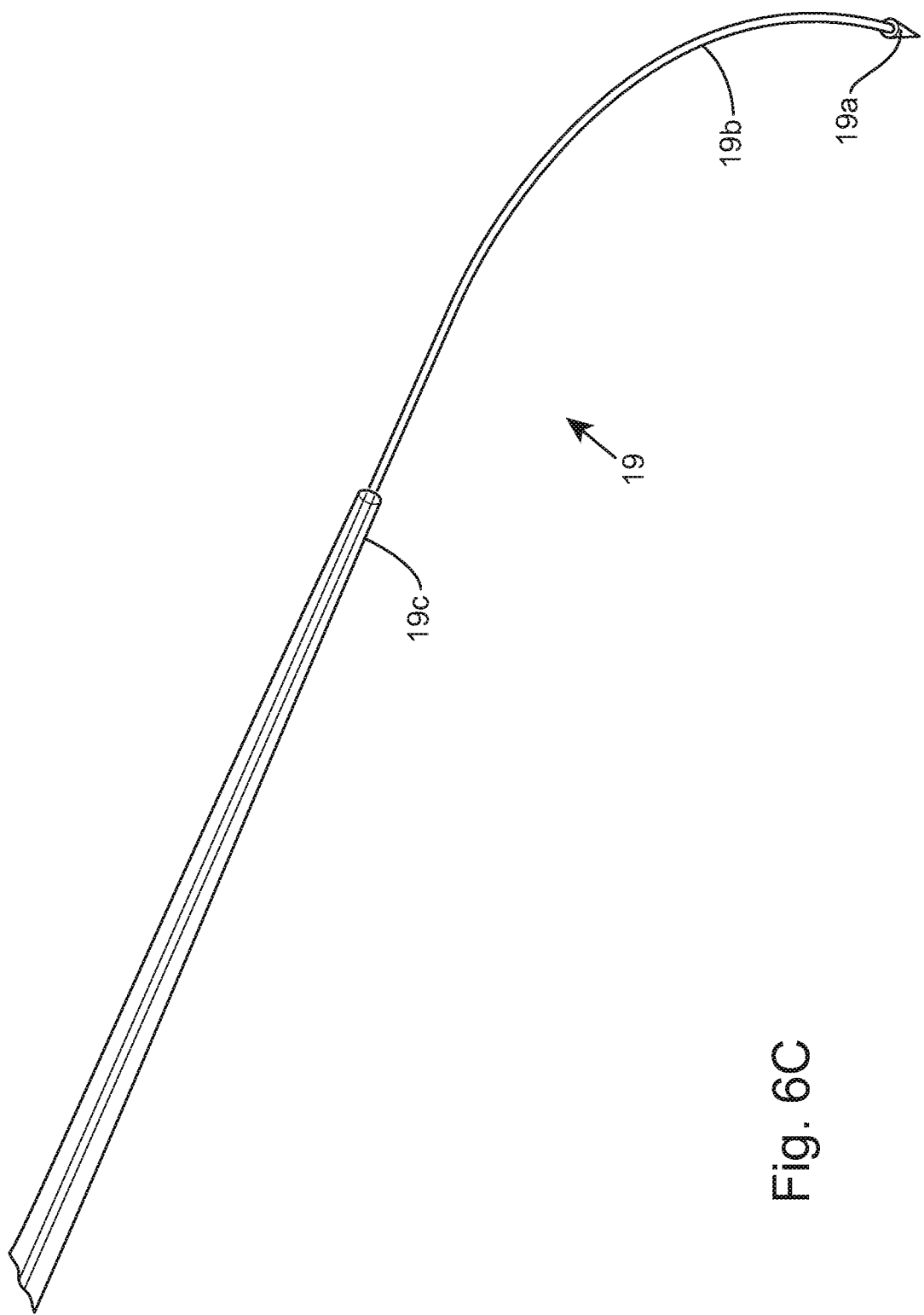

Fig. 7D″ 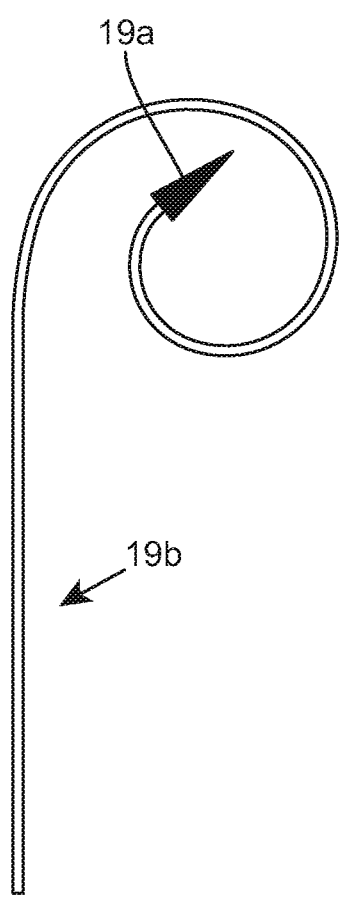

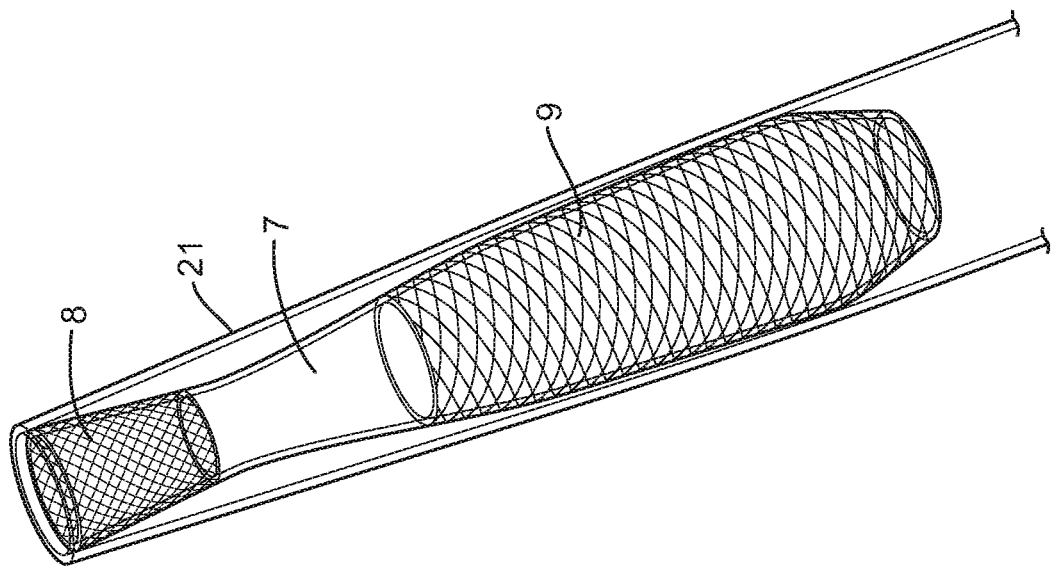
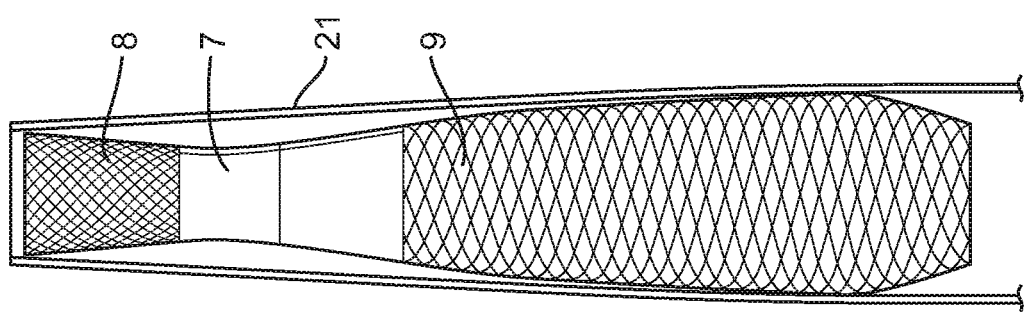

Fig. 16′
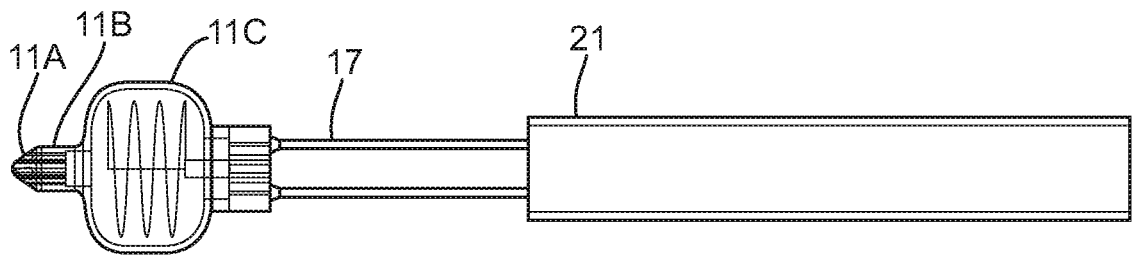
Fig. 16″
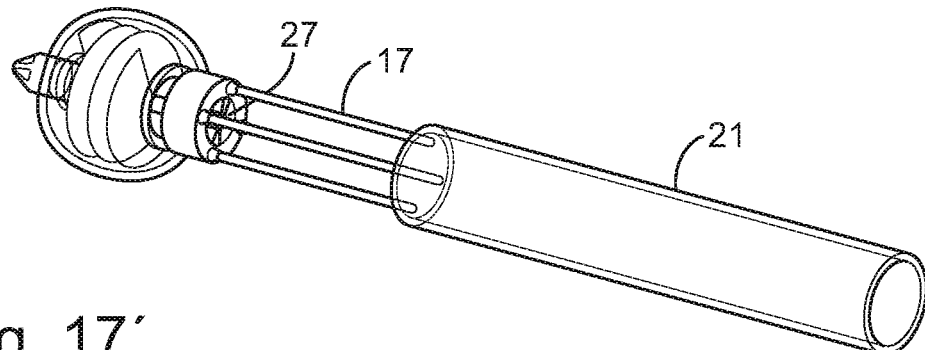
Fig. 17′
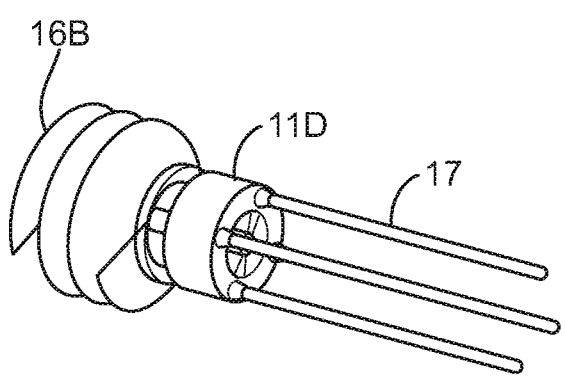
Fig. 17″
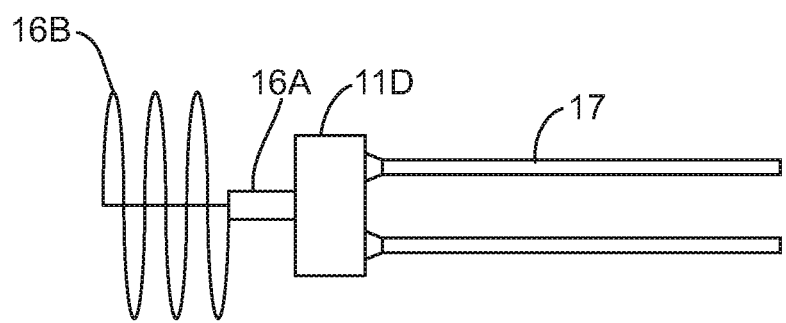

Fig. 18′
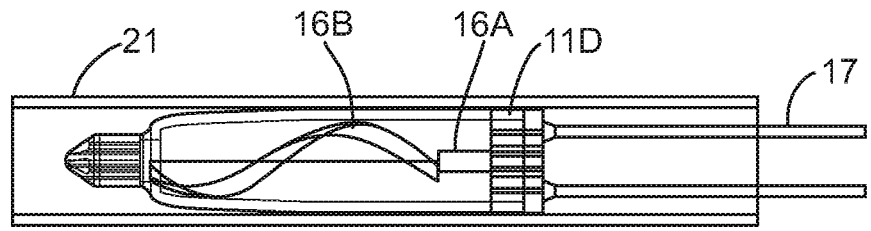
Fig. 18″
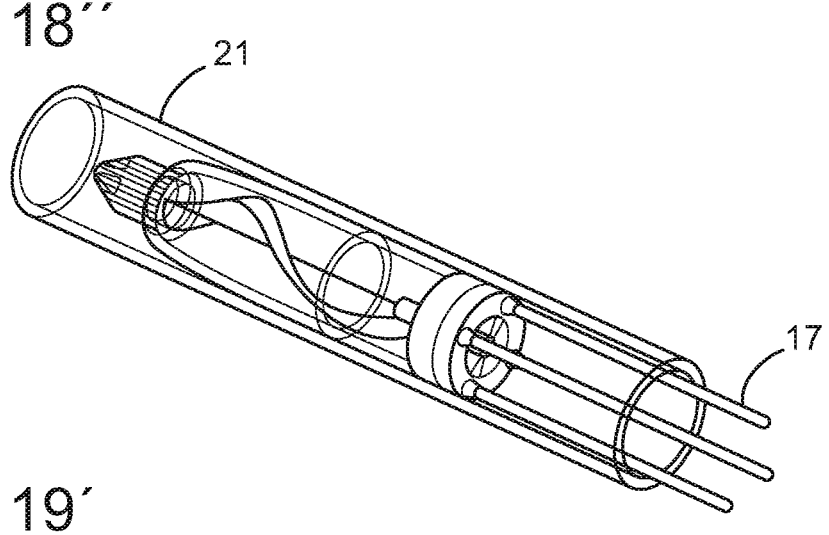
Fig. 19′
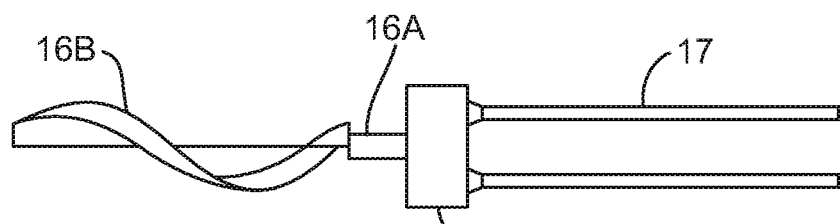
Fig. 19″
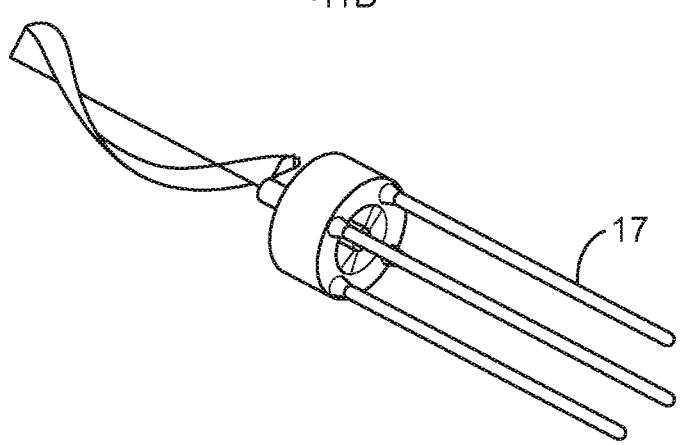

Fig. 20A′   Fig. 20A″   Fig. 20A‴
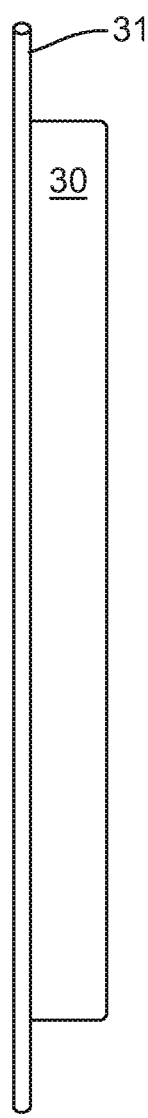 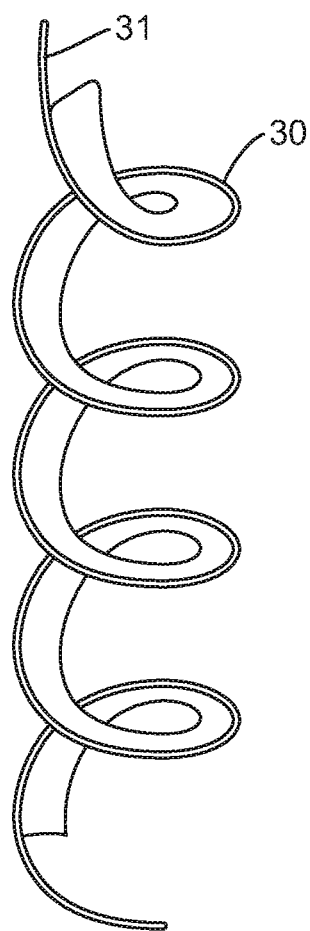 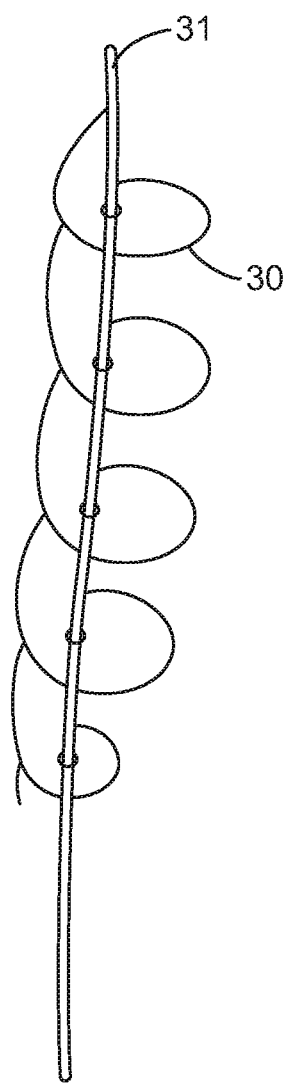

Fig. 20B′
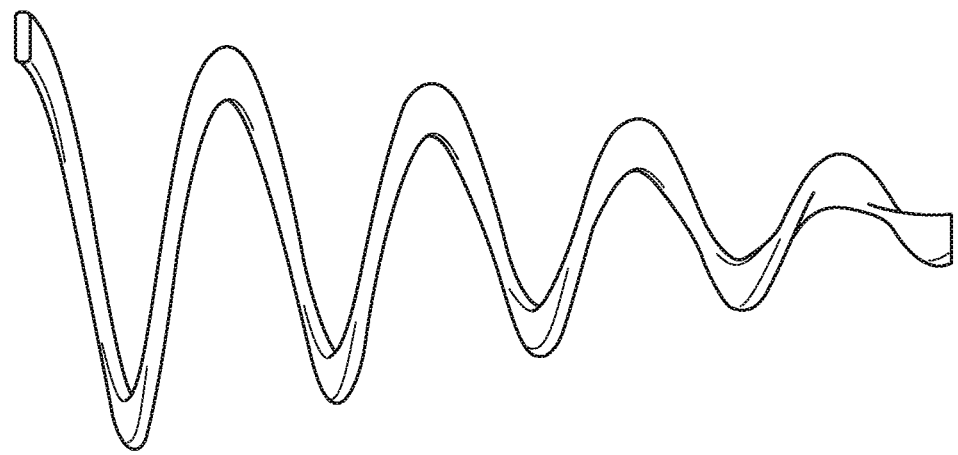
Fig. 20B″
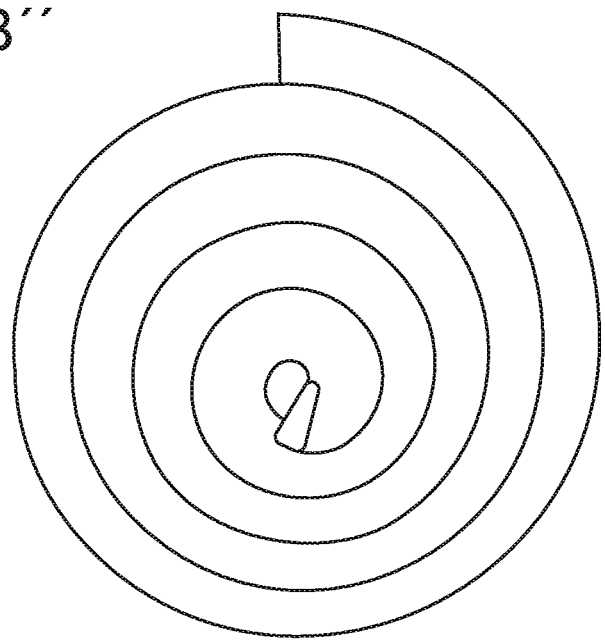

Fig. 21A′
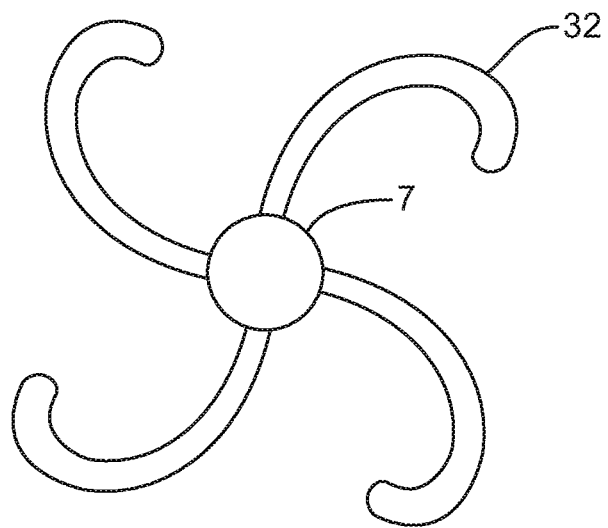
Fig. 21A″
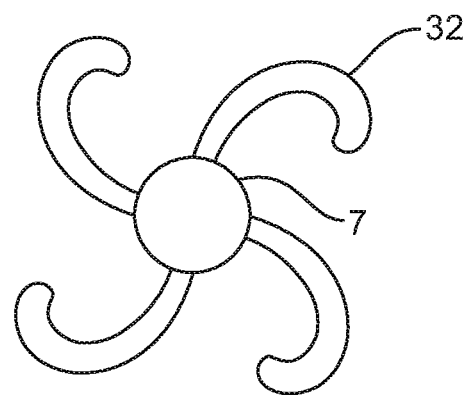

Fig. 21B″ 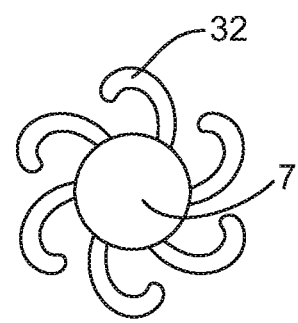

Fig. 21C′
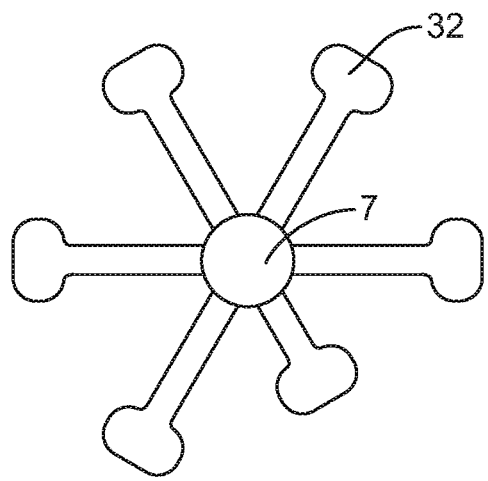
Fig. 21C″
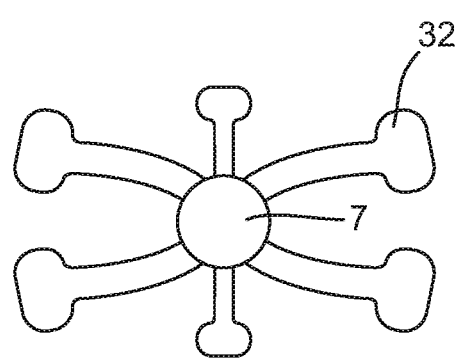
Fig. 21C‴
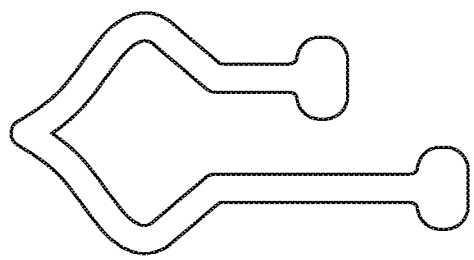

Fig. 21D′
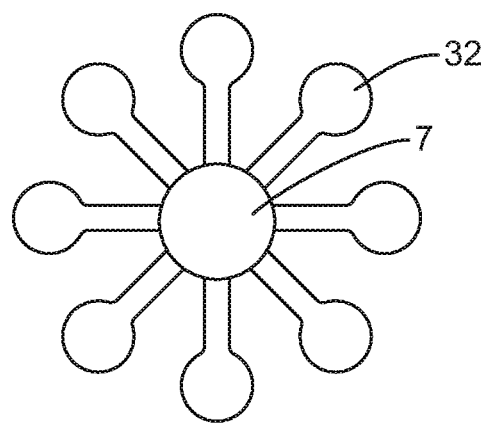
Fig. 21D″
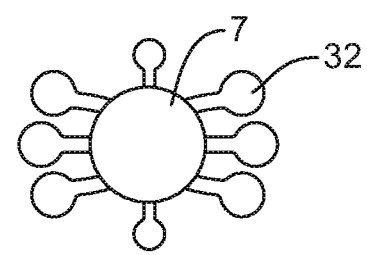

Fig. 21E′
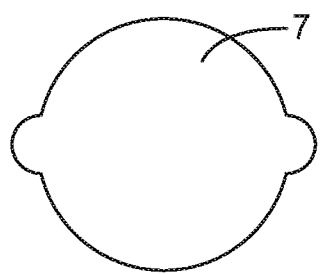
Fig. 21E″
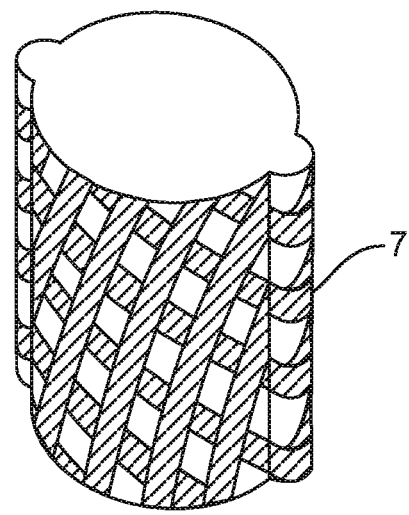
Fig. 21E‴
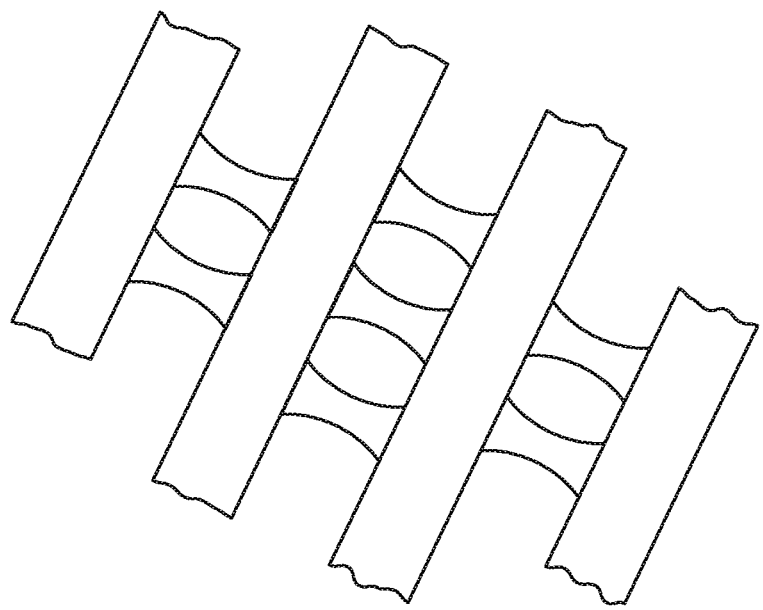

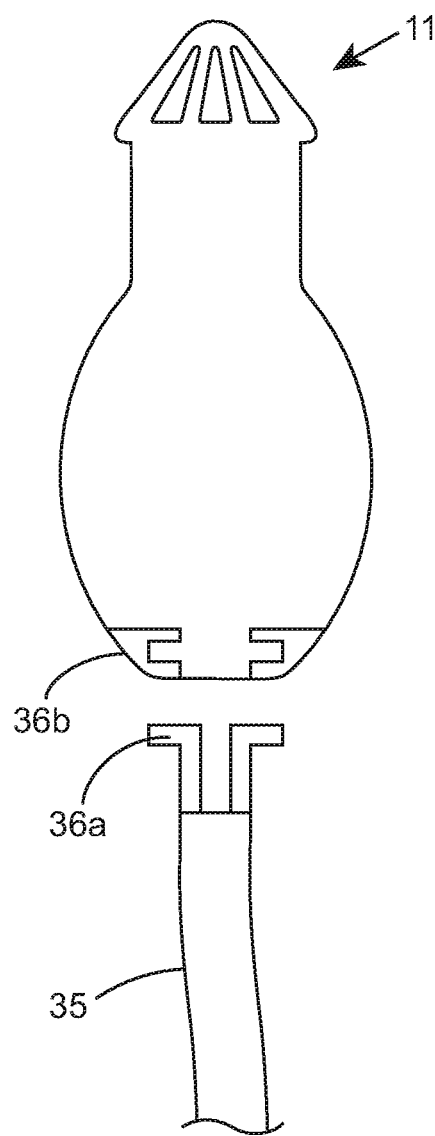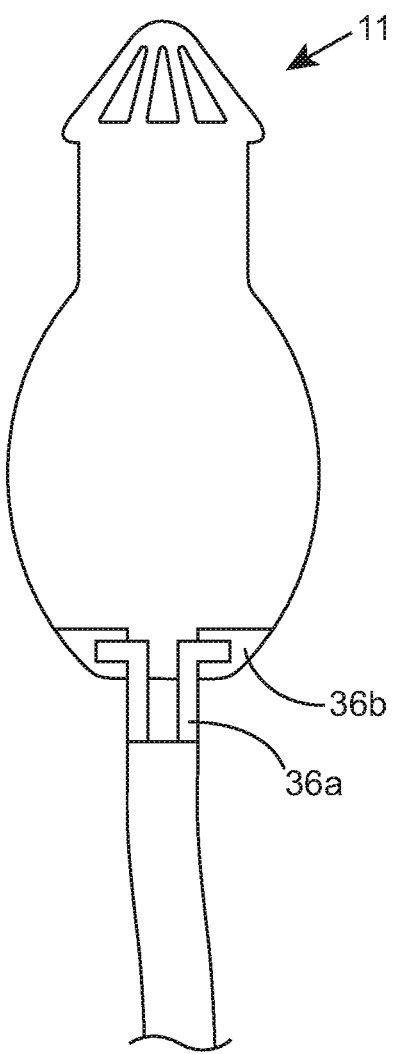

TRANSCATHETER SYSTEM AND METHOD FOR REGULATING FLOW OF FLUID BETWEEN TWO ANATOMICAL COMPARTMENTS

CROSS-REFERENCE TO RELATED APPLICATIONS

This application is a continuation of U.S. patent application Ser. No. 15/112,401, filed on Jul. 18, 2016, now patented as U.S. Pat. No. 10,130,742, which is a National Stage of International patent application No. PCT/EP2015/055578, filed on Mar. 17, 2015, which claims priority to foreign Norway patent application No. 20140353, filed on Mar. 17, 2014, and foreign United Kingdom patent application No. 1410320.4, filed on Jun. 10, 2014, the disclosures of which are incorporated by reference in their entireties.

FIELD OF THE INVENTION

The present invention generally relates to the field of medical devices and surgery devices. More specifically, the present invention relates to a transcatheter system and corresponding devices and methods of treatment. The present invention is particularly useful as a mechanical circulatory support system for example for the treatment of circulatory collapse, heart failure and heart conditions requiring a circulatory assist device but also has a wider variety of applications.

BACKGROUND

Examples of mechanical circulatory support systems (MCS) include ventricular assist devices (VADs). A VAD is a mechanical pumping device capable of supporting heart function and blood flow. Specifically, a VAD helps one or both ventricles of the heart to pump blood trough the circulatory system. Left ventricular assist devices (LVAD), right ventricular assist devices (RVAD) and biventricular assist devices (BiVAD) are currently available. Also, circulatory support systems may include cardiopulmonary support (CPS, ECMO), which provide means for blood oxygenation as well as blood pumping. Such devices may be required during, before and/or after heart surgery or to treat severe heart conditions such as heart failure, cardiopulmonary arrest (CPA), ventricular arrhythmia or cardiogenic shock.

Traditionally, VADs are fitted during open-heart surgery through an incision in the chest and the procedure involves puncturing the apex of the left ventricle to re-route blood from the ventricle to the aorta through an external pump. An example of device used in surgical VAD is HeartMate II™. Such surgical procedures are clearly invasive and unsuitable for weaker and vulnerable patients as they involve a greater recovery time and carry the risks of infection and trauma. This particularly the case in the treatment of children for whom existing surgical equipments and devices are comparatively bulkier and more invasive, and a reduction of the size of the equipment is often difficult if not impossible in view of the equipment and procedure involved. Furthermore, these devices require the intervention from a team of skilled surgical staff in a hospital environment and are therefore less available and costly.

More recent procedures are non-surgical and involve the insertion of a VAD through a small incision made at the groin of the patient. A popular version of such so-called percutaneous VAD is the TandemHeart™ device. A tube is introduced trough an incision adjacent the groin of the patient and advanced along the femoral vein and inferior vena cava, across the intra-atrial septum and into the left atrium so that oxygenated blood from the left atrium is fed into a pumping device located outside the patient's body and recirculated through an outflow tube into the femoral artery. Although this device has shown promising results, it only provides short-term support (up to two weeks) and is unsuitable for long-term treatments. The external pump is bulky and requires patient's immobilization for as long as the device is fitted. Furthermore, there is a risk of life-threatening infection around the groin incision, which remains open during the treatment, and of considerable bleeding from a major artery. In addition, the tube of the TandemHeart™ ends in the left atrium from which blood is pumped out and led outside the patient's body. This type of blood inlet system can potentially become hindered, if not blocked, if surrounding tissues are accidentally sucked in, thereby resulting to a loss of efficiency.

Another popular percutaneous VAD is the Impella™ device, which is inserted into the femoral artery and descending aorta. The Impella™ device comprises an elongated end, which is implanted across the natural aortic valve, with a blood inlet placed in the left ventricle and a blood outlet above the aortic valve. A pump circulates blood from the inlet to the outlet. The driveline is externalised through the femoral artery during use and the same limitations apply as with TandemHeart™ and other current percutaneous MCS systems. This device is approved to provide support for up to a week. There is therefore a need for a device with reduced risk of infection and bleeding and increased mechanical stability which can be used as part of a short-term "bridge to recovery" treatment or as a long-term treatment including patient mobilisation. In addition, the efficiency of the pump is limited because it is not possible to insert a pump of the size required to provide a suitable blood flow using percutaneous arterial access. Presently, the problem of limited pump capacity and duration with percutaneous MCS is solved either by inserting larger intracorporeal pumps surgically or by choosing an extracorporeal pump, with all the potential problems are described above.

Known mechanical circulatory support systems are life-saving. However, they remain costly, complex and have limited clinical potential with a majority of patients still passing away unaided.

Currently available percutaneous treatments rely on the main structures of the patient's anatomical vascular structure to be undamaged. However, many heart patients are children with congenital heart defects or elderly patients often with anatomical and vascular anomalies, such as calcifications and valvular disease. With surgery, such limitations may be overcome but benefit is hampered by the risk associated with surgical trauma. There is therefore a need for a procedure and device that can safely and predictably be deployed by percutaneously achieving access from one anatomical structure to another as this will allow for safe delivery of more efficient pumps without surgical trauma.

It is an object of this invention to mitigate problems such as those described above.

SUMMARY OF THE INVENTION

According to a first aspect of the invention, there is provided a transcatheter system comprising an intracorporeal connector for fluid communication between two anatomical compartments through at least one anatomical wall.

More particularly, the connector is adapted to receive an intracorporal flow regulating device.

Within the context of the invention, transcatheter includes percutaneous, trans-atrial, trans-femoral (through the leg), trans-apical (in the chest between the ribs), and trans-aortic (in the upper chest). Preferred embodiments are percutaneous systems, devices and methods.

The system according to the present invention is a transcatheter system and there is therefore no need for invasive and traumatic open surgery (as required for example to install a HeartMate™ system). Furthermore, both the connector and the flow regulating device are intracorporeal so that no major external parts are required. There is no need for complete patient immobilisation, as it is the case with a TandemHeart™ system, in which an extracorporeal pump is required. The system can therefore be used for short-, medium- and long term treatment. In addition, by connecting two anatomical compartments through one or more anatomical walls, the system can by-pass defective or anomalous anatomical parts. Rather than fixing or replacing existing problematic anatomical parts, the system according to the present invention effectively creates a new pathway for fluid circulation. This is therefore the basis for a more forgiving and versatile procedure.

The connector is able to preserve the integrity of the anatomical structure and tissues against the pressure exerted by the fluid (blood) flow and the flow regulating device, thereby preventing the collapse of the compartment(s).

In a preferred embodiment, when the flow regulating device is coupled to the connector, fluid can flow from the first compartment to the second compartment, and when the flow regulating device is not coupled to the connector, fluid cannot flow from the first compartment to the second compartment. The flow regulator device therefore functions as an actuator for the connector so that in the absence of the flow regulator device, fluid cannot flow between the compartments. The connector is inserted via percutaneous or transcatheter insertion, followed by the flow regulating device, also inserted via percutaneous or transcatheter insertion. Thus, the flow regulating device is coupled to the connector in situ. This is a marked difference with known systems either using an extracorporeal pump or in which the VAD is assembled outside the patient's body, then inserted as one bulky device. The present invention is particularly advantageous in that the intracorporeal assembly allows the use of smaller components for a minimally invasive procedure. In addition, this procedure is ideal for smaller patients, for example for paediatric applications. It is also interesting to note that the flow regulating device and/or the connector can be collapsible as will be described below in further detail.

The present invention is particularly advantageous when one or both compartments are compartments of the circulatory system. The preferred embodiment concerns a left atrium-aorta procedure. However, other compartment pairs are envisaged including, but not limited to, right ventricle-aorta, left ventricle-aorta, right atrium-vena cava superior, left atrium-aorta descending, left atrium-aorta ascending, right ventricle-pulmonary artery The present invention is particularly useful for use in the treatment of heart failure, diastolic heart failure, systolic heart failure, left ventricle failure, right ventricle failure, paediatric heart anomalies and/or shunts. Alternatively or additionally, one or both compartments are compartments within the thoracic cavity or the abdomen.

Preferably, the at least one anatomical wall is an outer wall of the compartment. For example, where the treatment is applied to the heart, then the artificial fluid passageway is an extra-cardiac passageway. Within the context of the invention, the expression "extra-cardiac passageway" means between the inside of the heart and the outside of the heart.

The number of walls through which fluid communication is created depends on the compartments to be connected. For example, a left atrium to aorta connection involves puncture and fluid communication through two anatomical walls (i.e. the roof of the left atrium and the aortic wall), whereas a right to left atrium connection only involves one anatomical wall (i.e. the atrial septum). Fluid communication is established through internal anatomical walls and not through external walls such as skin tissues. Preferably, the anatomical compartments are separated by two anatomical walls. More preferably, the connector connects two anatomically non-adjacent compartments. This means for example two compartments in close proximity of each other, but not anatomically in direct contact. This may also include two compartments which are in anatomical contacts in some parts, but are connected with the system according to the present invention at a portion in which the two compartments are not in anatomical contact. By way of example, the aorta and the left atrium of the heart may be in anatomical contact in some parts, but the connection is made for example through the roof of the left atrium and the aortic wall, where these two compartments are not in anatomical contact.

Preferably, the connector comprises a neck for fluid passage from one compartment to the other and means for securing the neck across the anatomical wall. In use, the neck of the connector is preferably embedded across the anatomical wall(s) and, if applicable, across interstitial space between two anatomical compartments/walls. Preferably, the neck comprises means for securing or detachably securing the flow regulating device to the connector.

An embodiment of the neck may comprise a channel for fluid passage from one compartment to the other. Preferably, the fluid channel is positioned along the central longitudinal axis of the neck. The neck portion is preferably sealed so that there is no fluid lateral leakage into the anatomical wall(s) and/or into any space separating two anatomical walls.

The neck can be susceptible to be dislodged, not only from the patient's movement, but also from the heart beating mechanism itself and it is therefore preferable to include means for securing and/or anchoring the neck across the anatomical wall(s). Thus, the securing means may comprise an anchor extending from a first end of the neck. The anchor may be expandable. More preferably, in its securing position, the anchor lies substantially parallel to the anatomical wall. In a preferred embodiment, the anchor can extend substantially perpendicularly from a first end of the neck and lay substantially parallel to the anatomical wall. Preferably, the anchor will be located in the anatomical compartment into which the fluid is delivered. The anchor secures the neck, and therefore the connector, across the anatomical wall(s), but also assist in preserving the integrity of the anatomical wall(s).

In one embodiment, the (expanded) anchor is substantially in the shape of a disk. In another embodiment, the anchor comprises a plurality of deployable arms. The deployable arms are preferably curved or may comprise one or more elbows The connector may also be secured to the anatomical wall(s) for example by using a neck made of an expandable material so that the neck is inserted in an unexpanded state, and expands upon release to closely contact the opening through the anatomical wall(s).

Preferably, the connector comprises means for preventing tissue from hindering fluid passage through the neck. The fluid passage, in particular in the case where a pumping device is used, creates a suction of the surrounding tissues towards the connector neck. The prevention means may comprise a shield extending from a second end of the neck. The shield may be expandable. The shield prevents surrounding tissues from becoming trapped in the connector neck and from hindering fluid passage. This type of shield can also act as an additional means for securing the connector neck in its correct position. Preferably, the shield is located in the anatomical compartment from which the fluid is removed. Preferably, the shield in its expanded state is substantially umbrella- or bowl-shaped. This embodiment is advantageous in that the surrounding tissues do not rub directly against the shield and are not sucked into the shield, so that scratches and injuries can therefore be avoided. Mesh-type or grid-type materials are preferred so as to minimise the amount of foreign material introduced into the patient. The shield prevents hindrance from tissues, but also secures the connector through the anatomical wall and assists in preserving the integrity of the anatomical wall(s).

In one embodiment, the (expanded) shield is substantially in the shape of a bowl or umbrella. In another embodiment, the shield comprises a plurality of deployable arms. The deployable arms are preferably curved.

Although a preferred connector is described as comprising one anchor and one shield, connectors comprising one anchor or one shield, two anchors or two shields are also envisaged.

As explained above, the integrity of the anatomical wall(s) may become compromised due to the pressure exerted by fluid/blood flow and the flow regulating device. The system according to the present invention comprises means for preserving the integrity of the anatomical wall(s), as embodied for example by the anchor and the shield of the connector. The present invention is particularly valuable when working on fragile anatomical walls, such as the aortic wall. The aortic wall must be manipulated with the utmost care, as an aortic rupture or any embolization may have dramatic, if not a lethal, consequences. The present invention provides a method, system and devices which enable safe puncture, delivery, insertion and implantation.

In a preferred embodiment, the connector is made wholly or partly of a shape memory material. The non-expanded connector can therefore fit into a sheath for transcatheter introduction into the patient. Preferably, the anchor and/or the shield are made of shape memory material. The connector can be introduced in a non-expanded elongated state through a delivery sheath.

Preferably, the neck comprises a gate to selectively prevent or allow passage of fluid through the neck. In a closed state, the gate prevents passage of fluid from one anatomical compartment to the other. The gate may be actuated, opened and maintained in an open stated mechanically, for example by using a flow-regulating device as described below.

Preferably, the device comprises means for securing the flow regulating device to the connector. One embodiment of such securing means is a gate as described above, which closes around the neck of the flow regulating device. In another embodiment, the connector and the flow regulating device may comprise complementary securing means, such as screwing means, preferably located on the inner surface of the neck of the connector and on the outer surface of the intermediate portion of the flow regulating device.

In another embodiment, the anchor and/or the shield of the connector comprise a plurality of arms. The arms may extend from one or both ends of the neck to form an anchor and/or a shield. The arms may extend along the inner surface of the neck to form a screwing means for securing the flow regulating device to the connector.

The screwing means is particularly advantageous in that the flow regulating device can be (detachably) secured to the connector, but can also be used to assist advancement and positioning of the flow regulating device through the connector.

The connector may comprise means for sealing for preventing undesirable fluid flow at the coupling interface between the connector and the flow regulating device or securing means. In a preferred embodiment, the connector and the flow regulating device comprises complementary screwing means and the sealing means comprises a strip of sealing material mirroring the screwing contour of the screwing means. Thus, in use, the sealing means is sandwiched between the screwing means of the connector and the screwing means of flow regulating device.

In a preferred embodiment, the sealing means is expandable. In its expanded, the sealing means is in the shape of a substantially rectangular strip of sealing material. In its collapsed state, the sealing means is substantially screw shaped. The sealing means may be made of a flexible material and/or a shape memory material. The sealing means may comprise means for securing the sealing means to the connector and/or the flow regulating device.

In a preferred embodiment, the system further comprises an intracorporeal device for regulating the flow of fluid between the two anatomical compartments. This flow-regulating device may enable the fluid flow from one compartment to the other to be interrupted or initiated, or the fluid flow rate to be adjusted. This is particularly advantageous because the present system creates fluid communication through an artificial opening through an anatomical wall and there would therefore be no natural existing mechanism to regulate the flow of fluid between anatomical compartments. For example, in the circulatory system, blood circulation is regulated by the heart muscles and existing natural openings, such as the aortic valve or mitral valves. The present invention does not rely on these natural openings and does not seek to repair defective natural openings, but instead create a new artificial blood pathway.

Preferably, the flow regulating device comprises an actuator capable of allowing or preventing fluid flow through the intracorporeal connector. Thus, fluid communication from one anatomical compartment to the other through the connector can be activated or terminated using the actuator, preferably by opening or closing the gate of the connector neck. In a preferred embodiment, fluid communication is enabled when the flow regulation device is mechanically coupled to the connector device and fluid communication is terminated when the devices are separated from each other.

In a preferred embodiment, the flow regulating device comprises a first portion located in use in the first compartment, a second portion located in use in the second compartment, and an intermediate portion located in use through the anatomical wall(s).

Preferably, in use (i.e. when the flow regulating device is correctly implanted across the anatomical wall(s), the intermediate portion is located through and secured to the neck of the connector. More preferably, in use, the intermediate portion is located through the gate of the connector. In a preferred embodiment, the outer dimensions of the intermediate portion of the flow regulating device is substantially complementary to the inner dimensions of the neck of the connector.

Preferably, the first portion comprises one or more apertures for fluid communication between the first and second compartment. Preferably, the intermediate portion comprises a channel for fluid communication between the first and second compartment. Preferably, the second portion comprises one or more apertures for fluid communication between the first and second compartment.

In a preferred embodiment, when the intermediate portion of the flow regulating device is coupled to the connector, fluid can flow from the first compartment to the second compartment, and when the intermediate portion of the flow regulating device is not coupled to the connector, fluid cannot flow from the first compartment to the second compartment.

Preferably, the flow regulating device comprises a pump. Thus, parameters such as fluid flow rate and/or timing of fluid flow between the anatomical compartments, and/or volume of fluid can be adjusted. Preferably, the pump is located in the first portion of the flow regulating device.

The system may further comprise means for treating or processing the fluid. In some instances, the fluid, for example blood, may be defective or require treatment. If the circulated blood is lacking in oxygen it can be oxygenated. Means for oxygen delivery can be included in the flow-regulating device, preferably by attaching an external oxygenator line to the device where oxygen can be released through trans-membranous passage (membrane-oxygenation) or directly into the blood stream through microscopic openings (bubble-oxygenation).

Furthermore, the blood may be treated by delivering one or more drug compounds to the fluid or equally, one could envisage means for removing a component (such as a contaminant) of the fluid when it flows through the system according to the present invention. Such delivery and removal means could be a chemical filter, a membrane and/or one or more openings in the device attached to an externalised line for substance transport. Advantageously, the intracorporeal device for regulating the flow of fluid comprises the fluid treatment means. If required, the system may also remove oxygen and/or other gas from the fluid. Other treatments such as heating or cooling of the fluid can also be effected where required.

The fluid treatment means may enable the introduction of one or more drug compounds for treating the fluid or for delivery into one or both compartments and/or the introduction of one or more gas, for example oxygen. The flow regulating device may include a controller to adjust the treatment parameters, such as timing, concentrations and dosages. A slow release or controlled release mechanism for drug delivery is also envisaged.

Preferably, the system comprises means for securing the flow regulating means to the connector. The connector device and/or the flow regulating device may comprise one or more securing means for secured attachment to each other. The two devices may be detachably or non-detachably secured to each other. This securing means is particularly advantageous when there is a risk of the devices becoming accidentally disconnected because of anatomical movement (e.g. from the heart muscles), movement from the patient, and/or fluid flow.

In a preferred embodiment, the second portion of the flow regulating device comprises one or more flanges for abutting against the anatomical wall or the expandable anchor of the connector, thereby securing the flow regulating device to the anatomical wall(s) but also to the connector.

Preferably, the intermediate portion is made of an expandable material to closely contact the inner surface of the connector's neck, thereby securing the flow regulating device to the connector.

In a preferred embodiment, the first portion comprises a cross-section of larger diameter than the diameter of the cross-section of the intermediate portion. This feature is advantageous for at least two reasons. Firstly, the intermediate portion of smaller diameter is positioned through the anatomical wall(s) and/or the connector and can be secured into position by the first and second portions. Secondly, the fluid is sucked into the first portion of larger diameter and flows through the intermediate portion of smaller diameter, thereby creating a Venturi effect improving the pumping efficiency of the flow regulating device.

Preferably, the second portion is substantially cone-shaped so as to facilitate insertion of the flow regulating device into and through the connector and/or the anatomical wall(s) and to minimize the risk of trauma. More preferably, the second portion comprises a rounded distal tip for atraumatic insertion.

In a preferred embodiment, the flow regulating device is adapted to receive a guide wire therethrough. Preferably, the first portion, the second portion and/or the intermediate portion comprises an aperture to receive a guide wire therethrough. Preferably, the flow regulating device is adapted to receive a guide wire along its longitudinal axis. More preferably, the first portion, the second portion and/or the intermediate portion comprises a channel to receive a guide wire therethrough. Most preferably, the channel is positioned along the longitudinal axis of the flow regulating device.

In a preferred embodiment, the flow regulating device is collapsible. Preferably, the flow regulating device can be arranged in a first configuration for insertion through a sheath and in a second working configuration. Preferably, the flow regulating device comprises an outer casing. The outer casing is preferably made of a flexible material. This is particularly advantageous as it improves the potential size (and therefore the efficiency) of the pump for transcatheter delivery which may also improve the potential for employing transcatheter magnetic drive pumps for long term use.

In a preferred embodiment, the flow regulating device may comprise a rotatable shaft supporting at least one blade, said blade being adapted for extension in the longitudinal direction of the shaft into an insertion configuration. The blade is adapted for relaxation in the longitudinal direction of the shaft into a working configuration.

In the lateral direction of the shaft, the dimension of the blade may be greater in the working configuration than in the insertion configuration. Thus, the blade and hence the flow regulating device can easily be inserted through a sheath.

Preferably, the blade is a screw type blade. The blade may be one continuous blade and/or a serpentine type blade. Preferably, the blade is made of a resilient (memory) material so that the blade can be extended or stretched in the longitudinal direction of the shaft.

The flow regulating device in its insertion configuration may be delivered to its working position through a delivery sheath or catheter. The flow regulating device expands into its working configuration as it exits the sheath, into its working position across the anatomical wall(s). In a preferred embodiment, the shaft and blade assembly is comprised in a compressible or stretchable outer casing of the flow regulating device. The shaft and blade assembly can be stretched in the longitudinal direction into an insertion configuration so that the lateral dimensions of the blade are reduced.

In another embodiment, the flow regulating device comprises an inverted-screw pump. In this embodiment, screws or blades are formed on a rotatable inner surface of the flow regulating device so that the fluid is suctioned from the first compartment to the second compartment.

Preferably, the flow regulating device is partly or wholly made of a magnetic material. For example, one or more elements of the device (e.g. casing, blade, magnetic bearing, magnetic drive etc) are made of a material with magnetic properties.

The present system is particularly advantageous when one or both anatomical compartments are compartments of the circulatory system. Compartments of the circulatory system include for example the left atrium, the right atrium, the left ventricle, the right ventricle, the aorta, the pulmonary artery, the vena cava as well as arteries, veins and other compartments of the peripheral vascular system. More preferably, the system according to the present invention creates fluid communication between two adjacent compartments.

Preferably, the fluid comprises or is blood, which may be oxygenated or deoxygenated. The system according to the present invention is advantageously used as a mechanical support system, preferably as a mechanical circulatory support system, such as a ventricular assist device.

In another embodiment, the connector and the fluid regulating device are constructed as a single device.

According to a second aspect of the invention, there is provided an intracorporeal connector as specified in any one of the preceding paragraphs.

According to a third aspect of the invention, there is provided an intracorporeal flow regulating device as specified in any one of the preceding paragraphs.

In a fourth aspect of the invention, there is provided a transcatheter insertion device comprising a guide wire comprising an integrally formed puncture head. The transcatheter insertion device enables the puncture of anatomical structures, for example anatomical wall(s) separating anatomical compartments, and is particularly advantageous for the puncture of outer walls of anatomical compartments with greater tissue resistance. The puncture head is preferably shaped so as to present an extremely sharp end to allow the practitioner for improved precision and control in a critical phase of the procedure. Such sharp end would normally not be used because of the risk of accidental puncture and/or injury. However, in the present invention the transcatheter insertion device is configured, as will be explained in further details below, to prevent such accidents.

In addition, the insertion device acts as a guidewire over which the various elements of the system according to the present invention, such as the intracorporeal connector device or the intracorporeal flow regulating device, can be inserted. Thus, it is possible to use a single device for both the puncturing step and the insertion/delivery steps of the procedure. In conventional methods, the puncture device would be performed using a separate puncture needle, which would be removed after puncture and followed with the introduction of a guide wire. This is not required with the present invention. In a known insertion system, a hollow needle is used to puncture the skin. A guide wire is inserted through the needle channel and the needle is removed leaving the guide wire in place. A catheter is then passed over the guide wire and the wire is removed, leaving the catheter in place. In the present invention, the puncture is made with the distal end of the guide wire, and in particular with the puncture head of the guide wire. This allows for a gradual, atraumatic and accurate incision to be made and this is particularly advantageous when puncturing outer walls of anatomical compartments, for example for cardiac to extra-cardiac puncture such as from one heart compartment heart into a major blood vessel.

Preferably, the puncture head comprises a solid distal tip. In other words, the puncture head is not hollow or does not comprises a distal aperture like in a conventional vascular puncture-needle as this would create an unnecessarily larger incision and often will require the use of undesired force for successful puncture. Larger incisions are not desirable where dangerously high blood flows are expected. The use of conventional needle is not recommended for anatomical wall such as the aortic wall in view of the risk of aortic rupture. In other conventional methods, a standard guide wire might be used to perform the puncture step. However, standard guide wires have a rounded or flat head which does not permit accurate puncture and may be dangerous if they accidentally deflect from the anatomical wall to be punctured. More preferably, the puncture head comprises a conical distal tip.

In a preferred embodiment, the diameter at the base of the conical tip is substantially the same as the diameter of the guide wire.

In a preferred embodiment, the guide wire is capable of coiling around the puncture head. Preferably, the guide wire comprises a flexible distal portion adjacent the puncture head, and a more rigid proximal portion. These features are particularly advantageous in the prevention of injuries due to the sharpness of the puncture head. Once the puncture has been performed, the puncture head advanced into the second compartment together with the dilator. When the dilator is removed, the flexible portion of the guide wire becomes unsupported and coils around the anchored puncture head, so as to provide an effective shield between the puncture head and surrounding tissues. More preferably, the guide wire is made of a shape memory material so that the guide wire can be configured into a shield surrounding the puncture head.

Preferably, the insertion device further comprises comprising a dilator. More preferably, the dimensions of the widest cross section of the puncture head are substantially the same as those of the distal end of the dilator.

Preferably, the insertion device comprises a delivery sheath. More preferably, the insertion device comprises an inner delivery sheath and an outer delivery sheath. In a preferred embodiment, the insertion device comprises a guide wire with a puncture head, a dilator, an inner delivery sheath and an outer delivery sheath.

The insertion device allows the puncture of anatomical walls and the insertion of a sheath or catheter through the patient's anatomy for subsequent introduction of transcatheter devices and the insertion device may further comprise means for guiding a sheath. The present invention is particularly advantageous in procedures involving insertion and implantation through two anatomical walls. This is because the insertion device can push one wall in contact with the other so that puncture and subsequent insertion and implantation are facilitated.

The system may be presented in the form of a kit comprising an intracorporeal connector, an intracorporeal flow regulating device and/or a transcatheter insertion device.

According to a fifth aspect of the invention, there is provided a transcatheter method for providing fluid communication between two anatomical compartments separated by at least one anatomical wall, the method comprising the steps of (a) puncturing the wall(s) separating the compartments, (b) inserting an intracorporeal connector through the puncture(s), and (c) coupling an intracorporeal flow regulating device to the intracorporeal connector. Preferably, step (c) is carried out intracorporeally.

Preferably, the puncturing step is carried out using an insertion device as specified in any one of the preceding paragraphs.

Preferably, the intracorporeal connector is a connector as specified in any one of the preceding paragraphs.

Preferably, the intracorporeal flow regulating device is a flow regulating device as specified in any one of the preceding paragraphs.

Preferably, the anatomical compartments are separated by two anatomical walls. More preferably, the two anatomical compartments are two anatomically non-adjacent. An advantage of the present invention is that fluid passage can be effected between two anatomically distinct compartments through an artificial fluid communication pathway.

Preferably, the method further comprises the step of pushing the two anatomical wall into contact prior to the puncture step (a) using the insertion device.

Preferably, the insertion step (b) is carried out using the insertion device. The puncture head of the insertion device can be used to perform step (a) to puncture the anatomical wall(s) and the guide wire to perform step (b) during the insertion procedure. Accordingly, in a preferred embodiment, the insertion device comprises a guide wire comprising an integrally formed puncture head.

Preferably, the method comprises the step of puncturing the wall(s) separating the compartments using the puncture head and guiding the intracorporeal connector through the puncture using the guide wire.

Preferably, the method further comprises the step of inserting and positioning the flow regulating device into coupling position relative to the connector.

Preferably, the method comprises the step of guiding the flow regulating device using the guide wire of the insertion device.

In a preferred embodiment, the intracorporeal connector and/or the intracorporeal flow regulating device are inserted in a collapsed state.

Preferably, the method further comprises the step of securing the connector to the anatomical wall(s).

Preferably, the method further comprises the step of securing the flow regulating device to the connector.

Preferably, the method further comprises the step of preventing tissue from hindering fluid passage through the flow regulating device.

Preferably, the method further comprises the step of regulating the flow of fluid by means of a pump comprised in the flow regulating device.

Preferably, the method further comprises the step of treating the fluid. In a preferred embodiment, the treatment of the fluid is carried out using the treatment means as specified above comprising the step of contacting the fluid with one or more drug compounds. Preferably, the method comprises the step of contacting the fluid with one or more gas, such as oxygen.

In a preferred embodiment, the method further comprises the step of detaching and retrieving the flow regulating device from the connector. The present invention is ideal for permanent or semi-permanent applications. However, in some circumstances, the flow regulating device may need to be retrieved for example for replacement and/or repair.

Preferably, the step of detaching and retrieving the flow regulation device is carried out using a retrieval device. More preferably, the retrieval device comprises means for grabbing the flow regulating device.

Preferably, one or both compartments are compartments of the circulatory system. More preferably, one of the compartments is the left atrium of the heart and/or one of the compartments is the aorta. Most preferably, the anatomical walls are the roof of the left atrium and the aortic wall.

According to a sixth aspect of the invention, there is provided a method for inserting a transcatheter system, comprising the step of puncturing at least one anatomical wall separating two anatomical compartments using an insertion device as described above.

Preferably, the anatomical compartments are separated by two anatomical walls. More preferably, the two anatomical compartments are two anatomically non-adjacent.

Preferably, the puncture method comprises the step of inserting the insertion device into the patient's circulatory system until the puncture head abuts the anatomical wall to be punctured.

Preferably, the puncture method comprises the step of pushing the two anatomical compartments into contact with each other using the insertion device.

Preferably, the puncture method comprises the step of puncturing the wall(s) separating the compartments using the puncture head and guiding a percutanous device(s) through the puncture using the guide wire.

Preferably, the puncture method comprises the step of preventing the puncture head from causing trauma to the patient's anatomy.

Preferably, the puncture method comprises the system is inserted through the femoral artery and/or inferior vena cava.

Preferably, one of the compartments is the left atrium of the heart and/or one of the compartments is the aorta. More preferably, the anatomical walls are the roof of the left atrium and the aortic wall.

According to a seventh aspect of the invention, there is provided a device for coupling or uncoupling the flow regulating device to or from the connector. The (un)coupling device comprises means for detachably coupling with the flow regulating device. Thus, the (un)coupling device can grab the flow regulating device for coupling or uncoupling and for implantation or retrieval of the flow regulating device. Preferably, the coupling means comprises one or more tabs capable of engaging with the flow regulating device.

Preferably, the (un)coupling device comprises means for remotely controlling the coupling means so the (un)coupling device can be remotely controlled to selectively grab or release the flow regulating device. Preferably, the coupling means is capable of rotation, so that it can be remotely controlled to selectively screw or unscrew the flow regulating device from the connector.

Preferably, the (un)coupling device comprises a catheter and a distal coupling means. Preferably, the catheter comprises one or more elbows so that the catheter can be advanced through the patient's anatomy without kinking.

The system and devices according to the present invention are particularly advantageous when used for the treatment of heart failure, diastolic heart failure, systolic heat failure, left ventricle failure, right ventricle failure, paediatric heart anomalies and/or shunts.

The present invention also concerns a transcatheter method for creating an artificial communication between two separate compartments through an anatomical wall (as opposed to a natural existing anatomical opening) comprising the step of using the transcatheter insertion device as described above, a transcatheter method for treating and/or processing a fluid comprising the step of using a flow regulating device as described above, a method for inserting an intracorporeal connector as described above, a method for inserting an intracorporeal flow regulation device as described above. Other methods relating to the present invention will be described below by way of example.

Within the context of the invention, the term "percutaneous" is used with reference to any medical procedure where access to inner organs or other tissue is done through a puncture and/or incision through the skin (and/or the vascular system) for example into the circulatory system, as opposed to an open surgery procedure. Thus, a percutaneous method involves the percutaneous delivery of elements and may involve an incision (for example with a scalpel) to enable percutaneous delivery. In a preferred embodiment, the method provides transcardiovascular delivery of one or more devices for establishing fluid communication between anatomically separate but adjacent thoracic organs, after gaining access to the vascular system by a puncture or incision. The puncture or incision may be made at various sites where intravascular access is possible, for example in the groin, axilla, chest or abdomen.

BRIEF DESCRIPTION OF DRAWINGS

The invention will be further described with reference to the drawings and figures, in which

FIGS. 6A to 6C are schematic representations of a percutaneous insertion device according to the present invention;

FIGS. 10A and 10B are schematic representations of an intracorporeal connector according to the present invention in a compressed state;

FIGS. 16' and 16" are a schematic representation of a second preferred compressible flow regulating device according to the present invention in an inserted state;

FIGS. 17' and 17" are a partial schematic representation of a compressible flow regulating device as shown in FIG. 15;

FIGS. 18' and 18" are a schematic representation of the compressible flow regulating device as shown in FIGS. 16' and 16" during insertion;

FIGS. 19' and 19" are a partial schematic representation of the compressible flow regulating device as shown in FIGS. 18' and 18";

FIGS. 20A' and 20A" and 20A''' are a schematic representation of a first sealing element for use in the present invention, in an expanded position and in two alternative working positions;

FIGS. 20B' and 20B" are a schematic representation of a second sealing element for use in the present invention;

FIGS. 23' and 23" are a schematic representation of a (un)coupling device according to the present invention.

DETAILED DESCRIPTION

Figure 1:
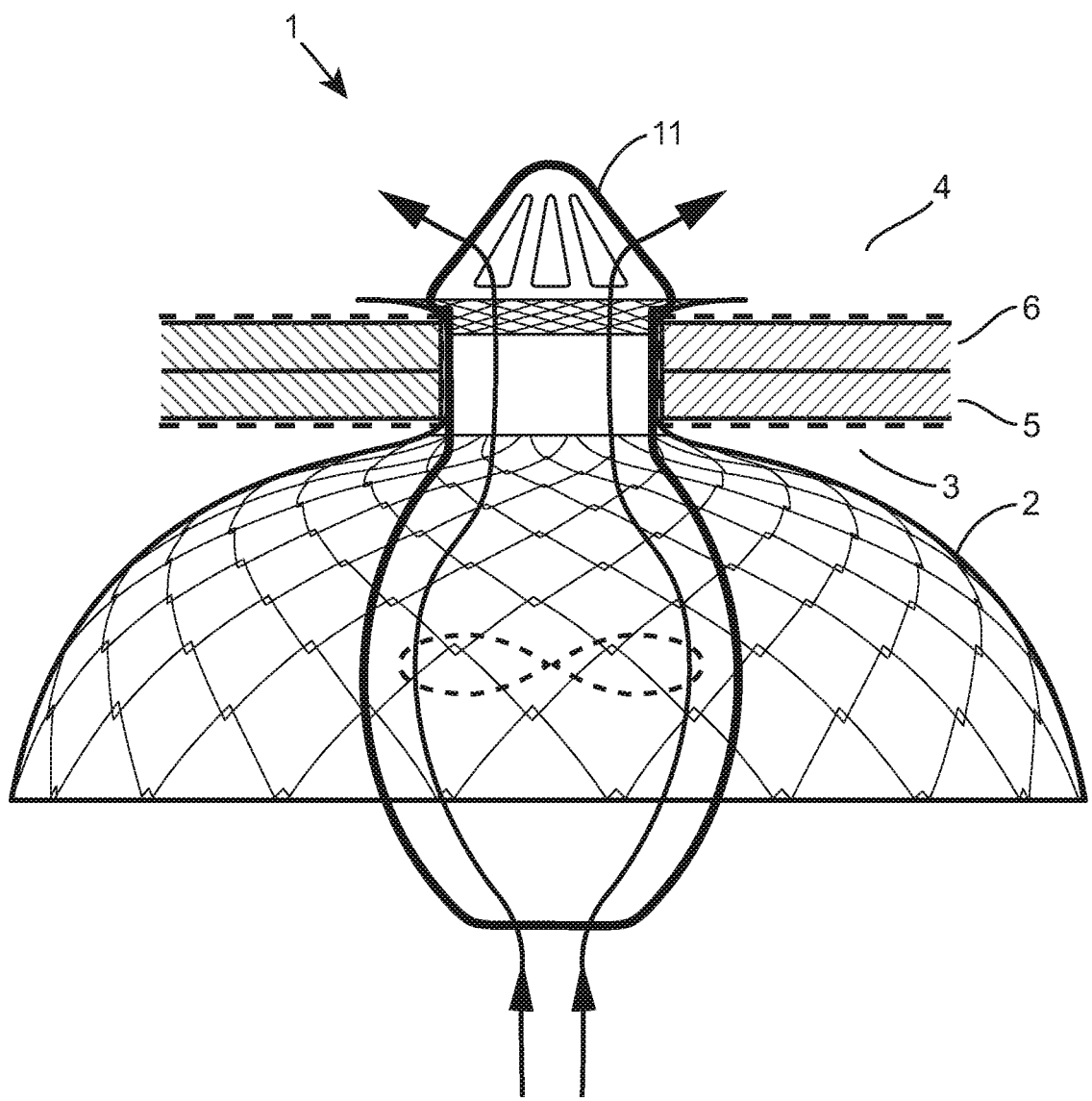
FIG. 1 is a schematic representation of an intracorporeal connector and a flow regulating device according to the present invention.
Figure 2A:
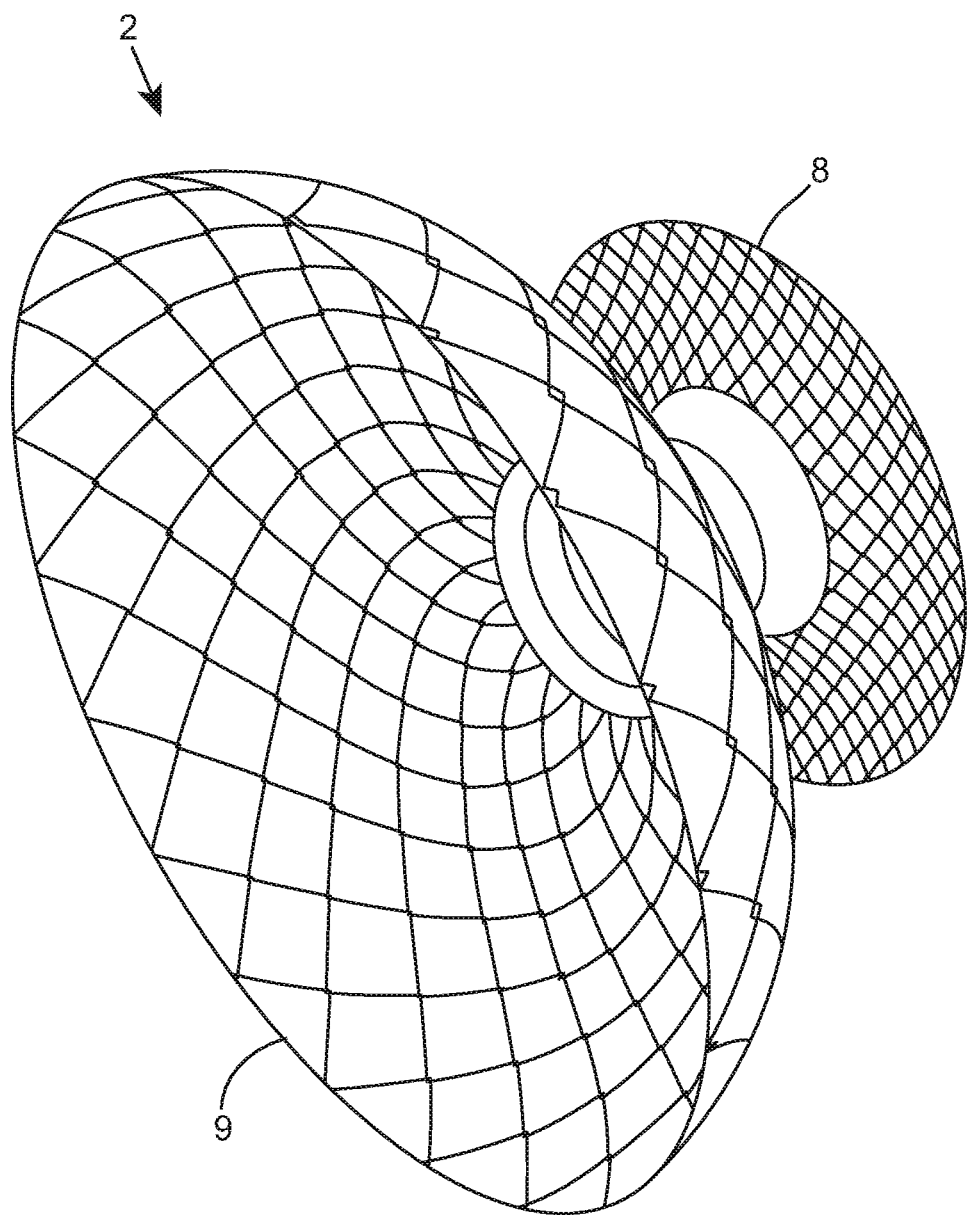
FIGS. 2A to 2C are schematic representations of an intracorporeal connector according to the present invention.
Figure 2B:
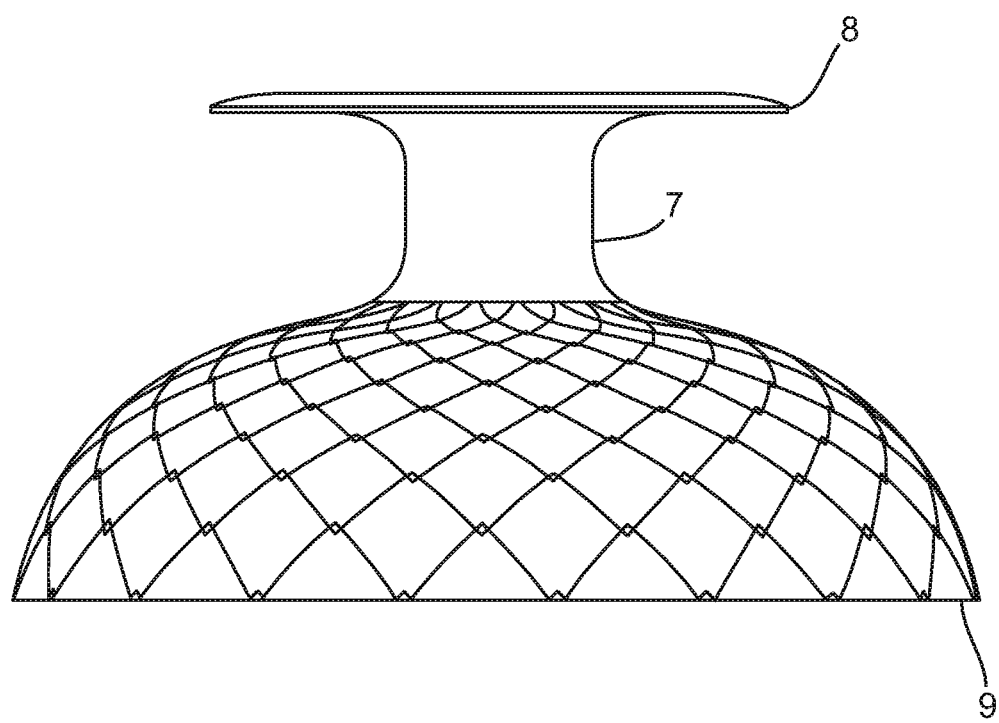
Figure 2C:
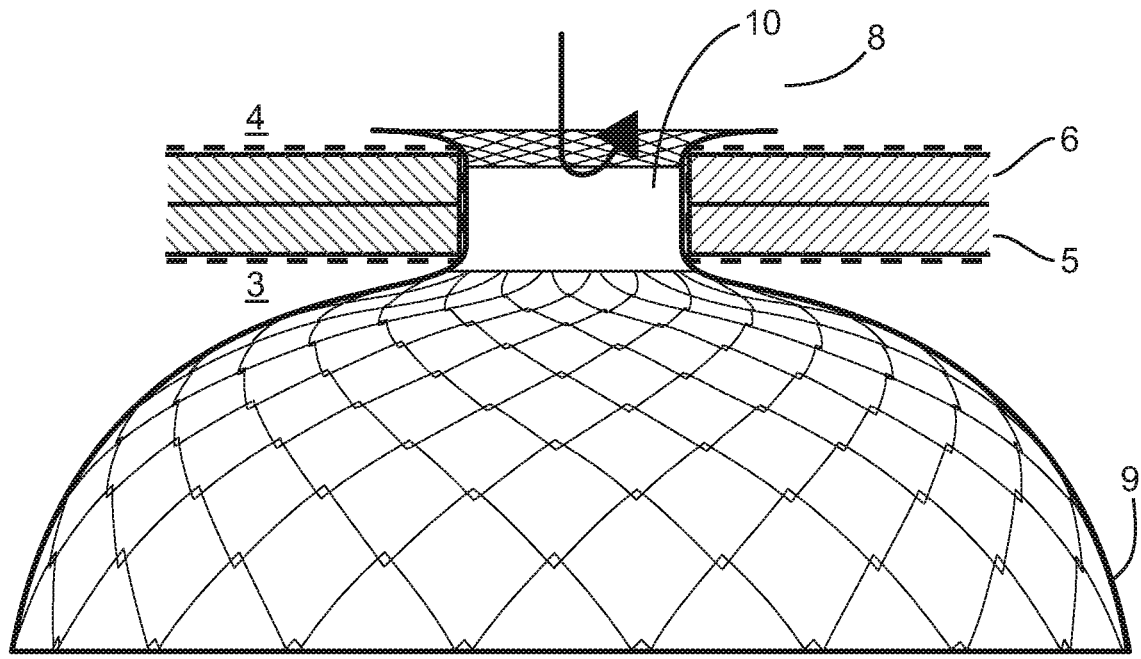

Referring to FIG. 1, there is illustrated a percutaneous system 1, in situ, comprising an intracorporeal connector 2 for fluid communication between two anatomical compartments 3,4 through at least one wall 5,6. In this illustration the first compartment is the left atrium 3 of the heart, the second compartment is the aorta 4, a first anatomical wall is the roof 5 of the left atrium 3 and a second wall is the wall 6 of the aorta 6.

The connector 2 is designed to preserve and support the structural integrity of the anatomical walls and compartments generally against the pressure exerted by the flood flow, but also during the insertion, implantation and retrieval processes of percutaneous devices.

An intracorporeal connector 2 according to the present invention will be described with reference to FIGS. 1 and 2A to 2C. The connector 2 comprises a waist or neck 7, and anchor 8 and a shield 9. Fluid, in this case blood, can flow across the neck 7 through a gate 10. The connector 2 is made of one or more biocompatible material and, if required, can be left in the patient after the treatment is completed.

Figure 21B:
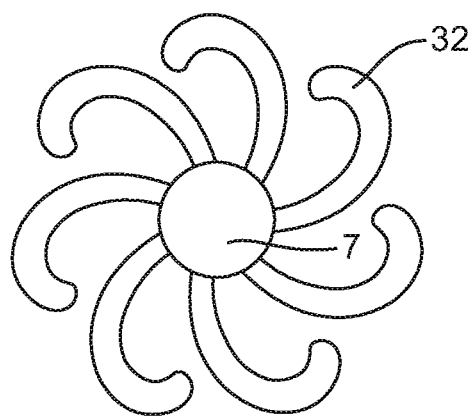
FIGS. 21A' to 21D" are top and bottom views of connector according to the present invention with an anchor and a shield comprising a plurality of arms.
FIGS. 21E' and 21E" and 21E''' are a partial schematic representation of a connector according to the present invention.

The neck 7 is typically made of a semi-flexible to substantially rigid material so that the pressure from the surrounding tissues does not compress the neck 7 and prevent fluid flow. The neck 7 comprises a biocompatible or surgical material, such as a metal or plastic material. The gate 10 is made of a resilient material (such as a plastic material or shape memory material) so that it can be in an open position allowing fluid flow or a closed position preventing fluid flow. The neck 7 may comprise a solid surface as shown in FIGS. 1 to 3 or may be made of a mesh-type surface as shown in FIGS. 21E' and 21E" and 21E".

Figure 3A:
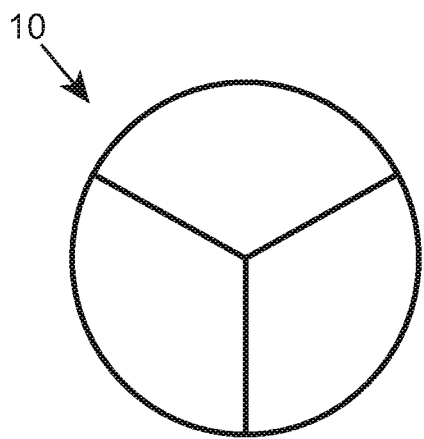
FIGS. 3A and 3B are schematic representations of gates for an intracorporeal connector according to the present invention.
Figure 3B:
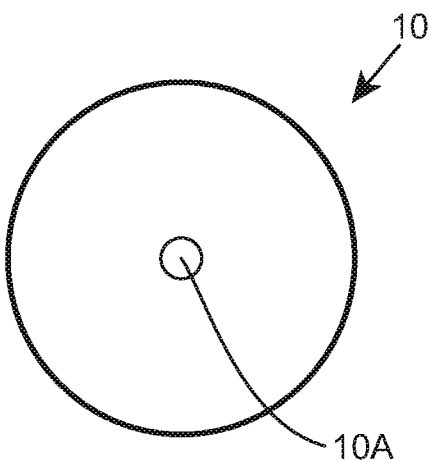

The gate 10 retains a closed position in the absence of action from an actuator. Two examples of gate 10 are shown in FIGS. 3A and 3B. In FIG. 3A, the gate 10 is made of several portions which can fit together in a closed position and can be pushed apart to create an opening. In FIG. 3B, the gate 10 comprises an opening 10A which prevents blood flow in a closed position, but can be stretched into an open position to allow blood flow.

In this embodiment, the system 1 connects the left atrium 3 to the aorta 4, which are relatively close to each other. However, where the compartments are oddly positioned or further from each other, the dimensions and shape of the neck 7 can be modified. For example, the neck 7 may be flexible enough to bend into a suitable position or articulated.

The anchor 8 extends from a first end of the neck 7. The anchor 8 is made of a resilient material, such as a shape memory material, so that it can be inserted in a folded state, as shown in FIGS. 10A and 10B and installed in an expanded state, as shown in FIGS. 1 and 2. In its folded state, the anchor 8 has a substantially cylindrical shape. In its expanded state, the anchor 8 can be deployed to prevent the connector 2 from moving within or being dislodged from the anatomical walls 5,6. In this embodiment, the anchor 8 in its expanded state is attached to and extends substantially perpendicularly from the end of the neck 7 so that it lies against and/or substantially parallel to the anatomical wall, here the aortic wall 6.

The shield 9 extends from the second end of the neck 7. The shield 9 is made of a resilient material, such as a shape memory material, so that it can be inserted in a folded state, as shown in FIGS. 10A and 10B and installed in an expanded state, as shown in FIGS. 1 and 2. The shield 9 comprises a mesh-type or grid-type material and can be made of the same material or a different material than that of the anchor 8. In its folded state, the shield 9 has a substantially cylindrical shape. In its expanded state, the shield 9 can be deployed to prevent surrounding tissues from being sucked towards and/or into the puncture through the anatomical walls 5,6. The shield 9 expands so that the surrounding tissues are not contacting the shield. This minimises the risk of injury due to suction through the mesh or rubbing against the shield. In this embodiment, the shield 9 expands into a substantially bowl-shape or umbrella-shape.

In the FIGS. 1 to 3, the anchor 8 is disk-shaped and the shield 9 is bowl-shaped. Both are made of a mesh-type material. In an additional or alternative embodiment, the connector 2 comprises a plurality of arms extending from one end or both ends of the connector 2 to form an anchor 8 and/or a shield 9. The arms may be curved and/or comprise one or more elbows and may be deployable or not. The arms may extend along the inner surface of the neck 7 to form a screwing means for securing the flow regulating device 11 to the connector 2. Examples of such connectors are shown in FIGS. 21A' to 21E'''.

A flow regulating device 11 according to the present invention will now be described with reference to FIGS. 4 and 5.

The device 11 comprises distal portion 11A, an intermediate portion 11B and a proximal portion 11C. In use, the distal end or tip of the distal portion 11A extends into one anatomical compartment 4 and the proximal end or tip of the proximal portion 11C extends into the second anatomical compartment. The intermediary portion 11C sits partially or completely in the neck 7 of the connector 2. Within the context of the invention, the term "distal" refers to the position closest to the patient and the term "proximal" to the position closest to the medical practitioner in the direction of insertion. In other words, the distal end of a device is inserted first and its proximal end is inserted last.

The device 11 comprises a channel (now shown) for blood passage through from the proximal portion 11C to the distal portion 11A of the device 11. The proximal end comprises one or more openings 12 to allow blood to enter the device 11, and the distal end comprises one or more openings 13 to allow blood to exit the device 11. The distal end of the device 11 is rounded to minimise trauma and pointed for ease of insertion.

Figure 5A:
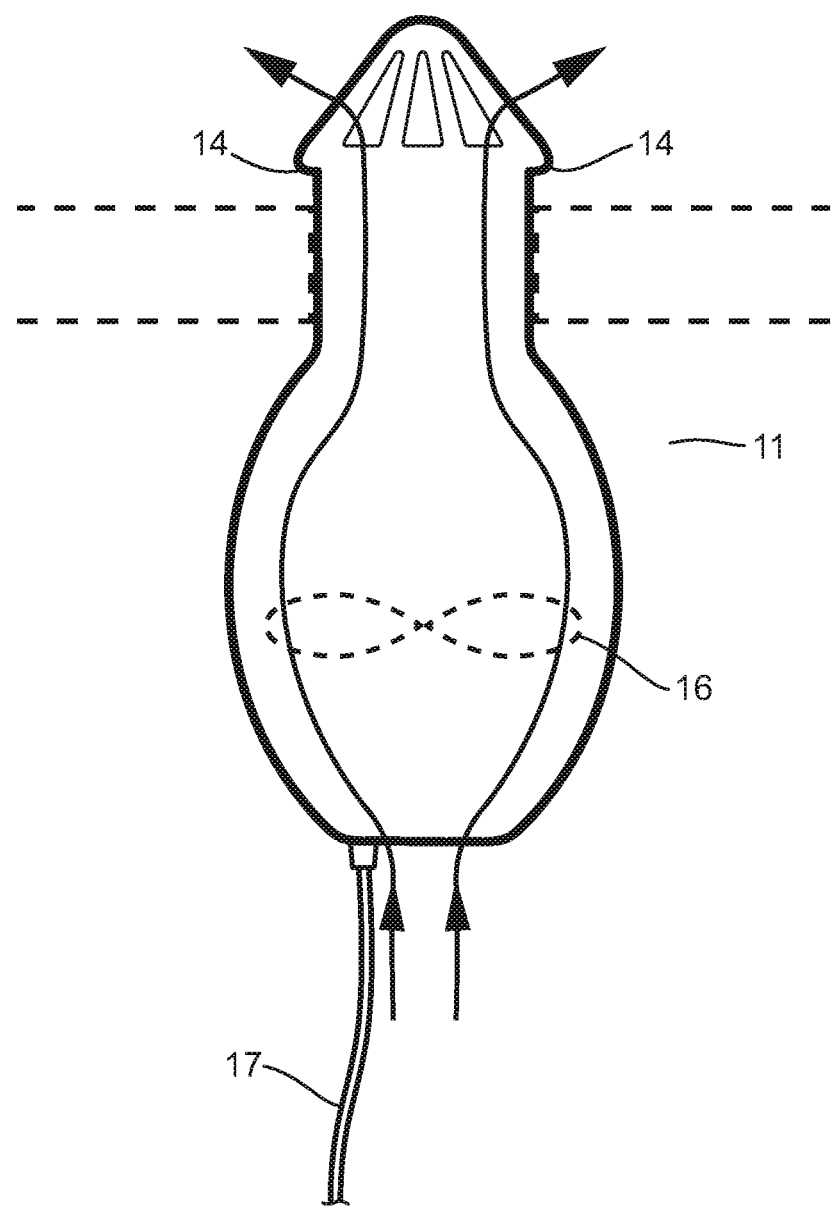
FIGS. 5A to 5C are schematic representations of an intracorporeal connector according to the present invention.
Figure 5B:
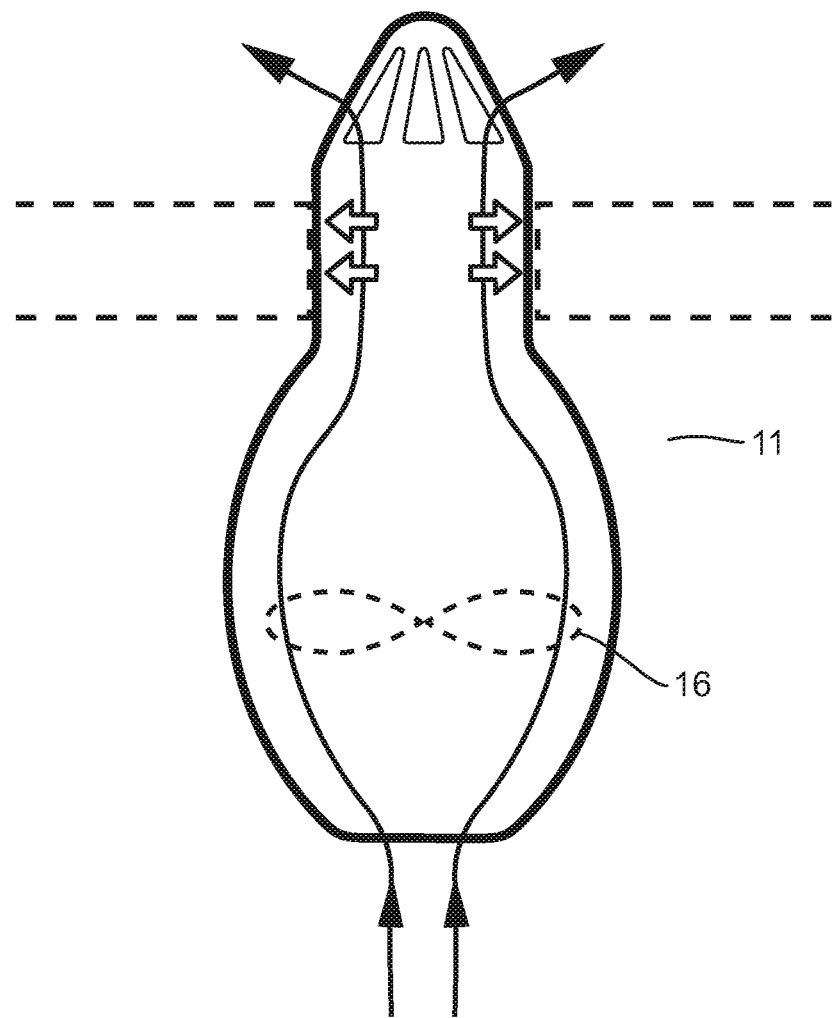
Figure 5C:
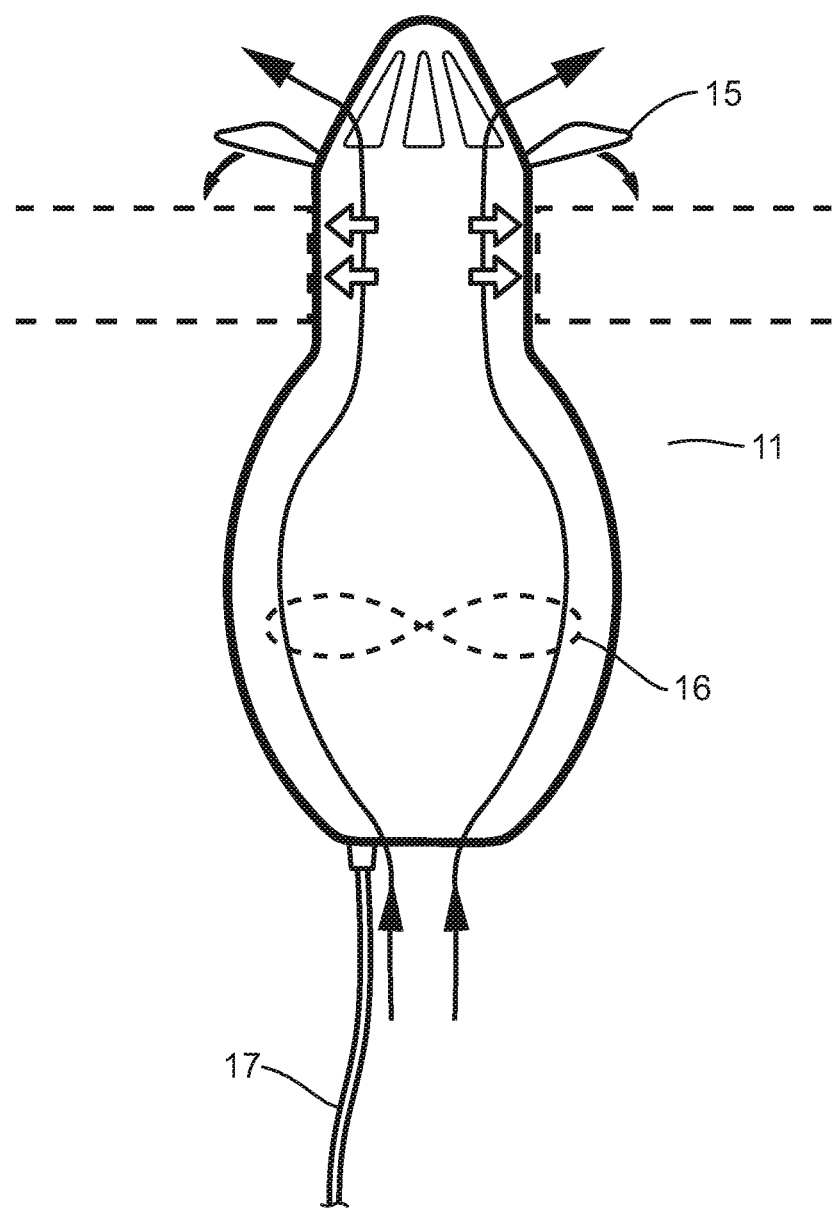

The flow regulating device 11 comprises means for securing the device 11 to the connector 2 and examples of such securing means are illustrated in FIGS. 5A to 5B. In FIG. 5A, the distal portion of the device 11 comprises one or more ribs 14 or tabs which prevent the device 11 from moving against the flow of fluid. In FIG. 5B, the intermediary portion 11B is partially or wholly made of a resilient or expandable material, which maintains the device 11 in place. The outer surface of the intermediary portion 11B can be modified so that it provides a better grip onto the connector neck's inner surface. In FIG. 5C, the distal portion 11A of the device 11 comprises flaps 15 or tabs which can be expanded to prevent the device 11 from moving against the flow of fluid or folded during the insertion procedure.

Another example of securing means is embodied by the gate 10. During the insertion procedure, the distal tip of the device 11 is pushed through and opens the gate 10, and, in its inserted position, the intermediary portion 11C sits partially or completely in the neck 7 of the connector 2, through the gate 10. Thus, the gate material resiliently closes around the distal portion 11B of the device 11 and secure the device 11 to the connector 2. In this description of the insertion procedure, the distal portion 11A or distal end of the distal portion 11A of the device 11 acts as an actuator to the connector 2, by opening the gate 10 and allowing blood to flow from the left atrium to the aorta.

Alternatively, or additionally, the connector 2 and the flow regulating device 11 can comprise complementary securing means, such as screwing means, located on the inner surface of the neck 7 of the connector 2 and on the outer surface of the intermediate portion 11B of the flow regulating device 11. The screwing means is particularly advantageous in that the flow regulating device can be (detachably) secured to the connector, but can also be used to assist advancement and positioning of the flow regulating device through the connector.

In another preferred embodiment, the connector 2 and the flow regulating device 11 can be coupled by means of a twist and lock mechanism, an example of which is shown on FIGS. 21E' to 21E'''. In this embodiment, the neck 7 may comprise two or more channels or longitudinal protrusions for locking.

The connector 2 can also comprise means for sealing for preventing undesirable fluid flow at the coupling interface between the connector and the flow regulating device or securing means. For example, the connector and the flow regulating device comprises complementary screwing means and the sealing means comprises a strip of sealing material mirroring the screwing contour of the screwing means. Thus, in use, the sealing means is sandwiched between the screwing means of the connector and the screwing means of flow regulating device.

An expandable sealing means can be used, which in its expanded configuration, is in the shape of a substantially rectangular strip of sealing material. In its collapsed state, the sealing means is substantially screw shaped. The sealing means can be made of a flexible material and/or a shape memory material. The sealing means may comprise means for securing the sealing means to the connector and/or the flow regulating device.

The flow regulating device 11 comprises a channel 34 through which the guide wire 19b is received. In a preferred embodiment, the channel 34 extends from the proximal end to the distal end of the flow regulating device 11. Preferably, the channel 34 extends along the central longitudinal axis of the flow regulating device 11.

The flow regulating device 11 comprises an internal pump 16. The pumping parameters can be adjusted by an intracorporeal or extracorporeal controller (not shown). In the case of an extracorporeal controller, wireless control is preferred. Current can be fed to the pump 16 through an electrical lead 17 or the device 11 can contain an internal battery. In the case of a chargeable battery, charging mechanisms which do no involve the insertion of further devices into the patient are preferred, for example, a magnetic charging mechanism. If the battery cannot be recharged, then the device 11 can be removed and replaced or discarded after use. The electrical lead 17 or other tubing may be used as a pull string to remove the device 11 from the patient after use or a dedicated pull string may be added.

If the fluid pumped from one compartment 3 requires treatment or processing before being delivered into the second compartment 4, suitable means (not shown) can be incorporated into the device 11. For example, a drug delivery device can contact the blood flowing through the device 11 with one or more drugs; or the blood can be oxygenated before exiting the device 11 using an oxygenating device or membrane. In the case of drug delivery, the device 11 incorporates a drug reservoir or be connected to an external drug reservoir. A slow- or controlled-release mechanism is also envisaged. The system 1 according to the present invention could also be regarded as an intracorporeal drug delivery system, in which a drug is delivered into a target compartment, with or without blood flow.

The flow regulating device 11 is self contained so that all the elements, including the pump 16, drug delivery or oxygenation devices, as required, are incorporated in the casing of the flow regulating device 11.

A preferred flow regulating device 11 for use in the present invention is described with reference to FIGS. 16' to 19". This device 11 is a variation of the device as described above and can comprise any feature relating to the device 11 as described in the preceding paragraphs.

The flow regulating device 11 comprises a distal portion 11A, an intermediate portion 11B and a proximal portion 11C. The proximal portion 11C forms a casing partially or wholly surrounding the pump 16. The proximal portion 11C further comprises a detachable base 11D. The base 11D can be attached by rotation, for example by screw or bayonet means. This detachable base 11D comprises one or more openings 27 so that fluid can flow into the base openings 27 from a first anatomical compartment, through the device 11 and exit through openings 13 at the distal portion 11A of the device 11 into a second anatomical compartment.

The base 11D comprises a rotatable shaft 16A supporting at least one blade 16B. The blade 16B is a screw type blade extending from the shaft 16A. The proximal end of the blade may be extend from the shaft 16A. The distal end of the blade 16B may be attached or not to the distal end of the proximal portion 11C of the device 11 or the proximal end of the intermediate portion 11B of the device 11. The screw blade 16B is arranged and constructed such that it can be extended or stretched in the longitudinal direction of the shaft 16A for ease of insertion through a working sheath 21.

In this extended configuration, the screw blade 16B is stretched longitudinally so that the overall diameter of the blade 16B is smaller than in the relaxed configuration. The blade 16B reverts to its original relaxed configuration, i.e. its working configuration, as it exits the sheath 21. In its working configuration, the overall diameter of the blade 16B is greater than in the stretched position. Thus, in the stretched configuration, the screw blade 16B can easily be inserted through a sheath 21 and in the working configuration, the size of the blade 16B is maximised for optimum capacity and efficiency. This also means that a blade 16B with a greater number of thread forms per unit length (and therefore greater efficiency) can be used. Any part of the device 11, in particular, the proximal portion 11C of the device 11 and/or blade 16B, can be made of a resilient (or shape memory) material, which may be the same or different. In a preferred embodiment, the extendable pump is surrounded by a proximal portion 11C of the device 11, and the proximal portion 11C is made of a resilient material such that it can be compressed to fit into a sheath and subsequently deployed use. In this embodiment, the base 11D is preferably made of a rigid material.

Figure 22:
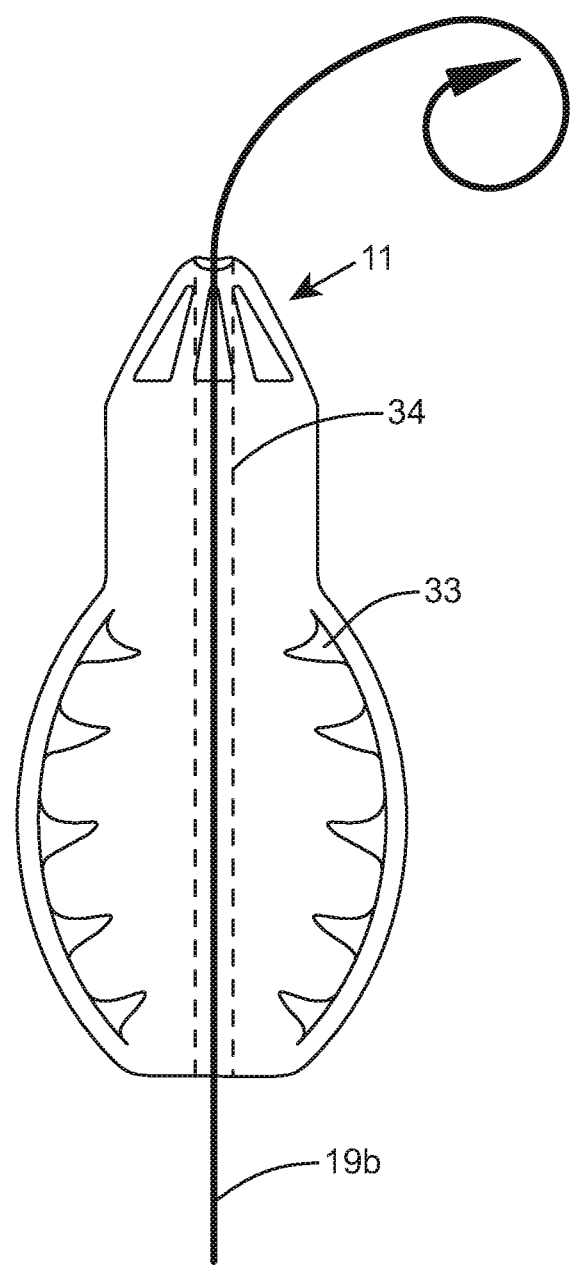
FIG. 22 is a schematic representation of an flow regulating device according to the present invention comprising an inverted screw pump.

In another embodiment as shown in FIG. 22, the flow regulating device 11 comprises an inverted-screw pump mechanism in which screws and/or blades 33 are formed on a rotatable inner surface of the flow regulating device 11 so that the fluid is suctioned from the first compartment to the second compartment. In this embodiment, blood flows centrally within the flow regulating device. This arrangement is also advantageous in that the/a guide wire can easily be positioned along the central longitudinal axis of the flow regulating device 11.

The base 11D can comprise a compartment (not shown) for including a pump motor, other elements required for the pump to function, fluid treatment and/or processing means as described above. Alternatively, the base 11D or proximal portion 11C may comprise one or more ridges for drug and/or oxygen delivery. The ridges can for example be disposed around the shaft 16A. Any connection 17 between the device 11 and outside the patient's body can be attached to the base 11D.

The principle of deployable percutaneous elements, such as expandable connectors and flow regulating devices, by-passes the current need for miniaturisation. In other words, instead of reducing the size (and therefore compromising capacity and efficiency) of the elements, full size elements can be inserted into the patient's vascular system through small incisions in a folded or compressed state, deployed at the correct location and subsequently removed from the patient in a folded or compressed state. This paves the way for a more versatile system in terms of size and shapes and children in particular would benefit greatly. This also means that, not only subcutaneous drivelines (similar to those used in connection with pacemakers) can be used, but also external drivelines and deployable elements can be inserted through the venous system. Thus, if major arteries can be avoided, the risk of infection and heavy bleeding is minimised.

Figure 6A:
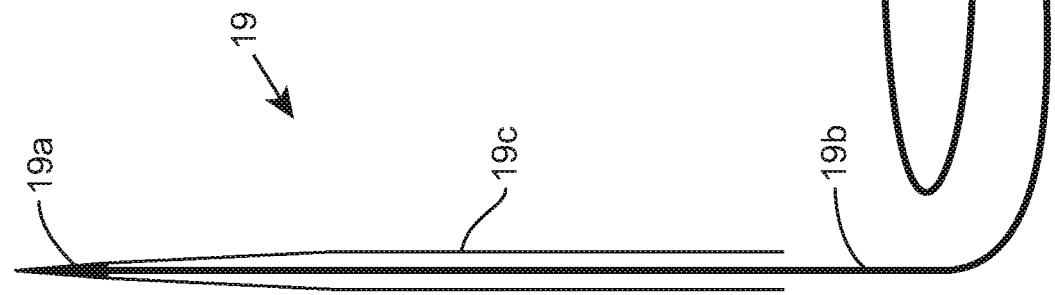
Figure 6B:
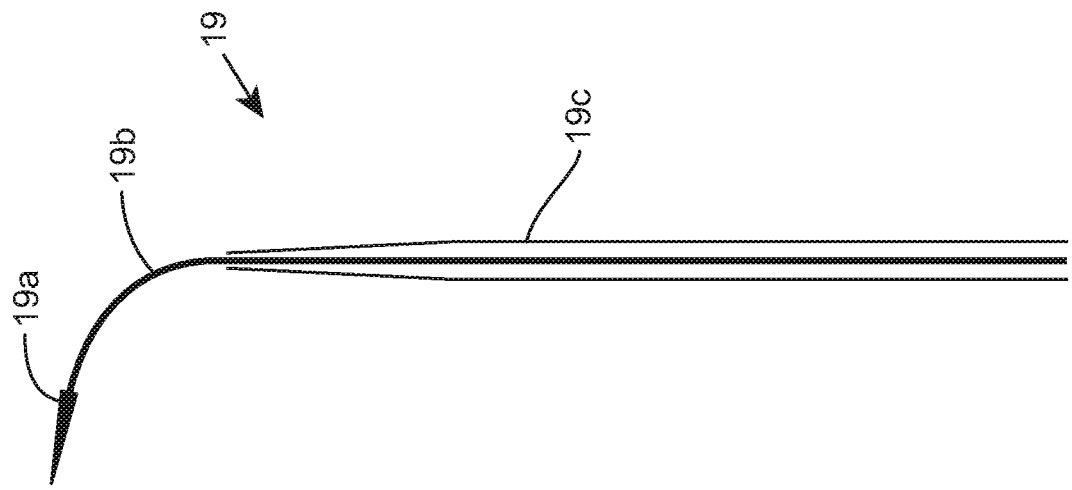

A percutaneous insertion device 18 according to the present invention will now be described with reference to FIGS. 6 to 8.

The percutaneous insertion device 18 comprises a puncture head 19a integrally formed with a guide wire 19b and a dilator 19c. The insertion device further comprises a working sheath 21 an outer sheath 23. The insertion device 18 is used to insert any device or element which may be required for the method according to the present invention.

As will be described in more detail below, the needle 19 and in particular the puncture head 19a is used to puncture one or more anatomical walls; the guide wire 19b to direct the elements during insertion; the dilator 19c to stretch punctures made by the puncture head 19a; the working sheath 21 to insert, deliver and position the devices of the system 1 and the outer sheath 23 to form a safe passageway for inserting the devices of the system 1.

In this embodiment, the puncture head 19a is connected to the distal end of the guide wire 19b for example by welding. The puncture head 19a has a solid tip, i.e. devoid of a hollow channel as observed in standard insertion or injection needles. The puncture head 19a is conically shaped and forms an extremely sharp tip. The diameter at the base of the conical puncture head 19a is larger than that of the guide wire 19b. The guide wire 19a is slidable through a dilator 19c. The diameter at the base of the conical puncture head 19a is substantially equal to that of the distal end of the dilator 19c so as to create a flush, smooth transition.

In an alternative embodiment (not shown), the diameter at the base of the conical puncture head 19a is substantially the same as that of the guide wire 19b so that the guide wire 19b is a tapered guide wire with a sharp conical tip. In this alternative embodiment, the puncture head 19a and the guide wire 19b are integrally formed. A diameter of the guide wire 19b is substantially equal to that of the distal end of the dilator so as to create a flush, smooth transition; although in this case, the dilator 19c may not be required as the tapered guide wire 19b can act as a needle.

The use of a sharp puncture head 19a at the distal end of the guide wire 19b allows the insertion device 18 to act as an atraumatic and accurate puncture device. These relative dimensions of the puncture head 19a, the guide wire 19b and the dilator 19c enable the size of the puncture to be gradually and gently increased.

The guide wire 19b preferably comprises two or three sections of different rigidity, for example a distal portion of relatively rigid material, an intermediate portion of flexible material and a proximal portion of relatively rigid material. These differences in rigidity enable the manipulation and guiding of the guide wire through the patient's anatomy.

Figure 7C:
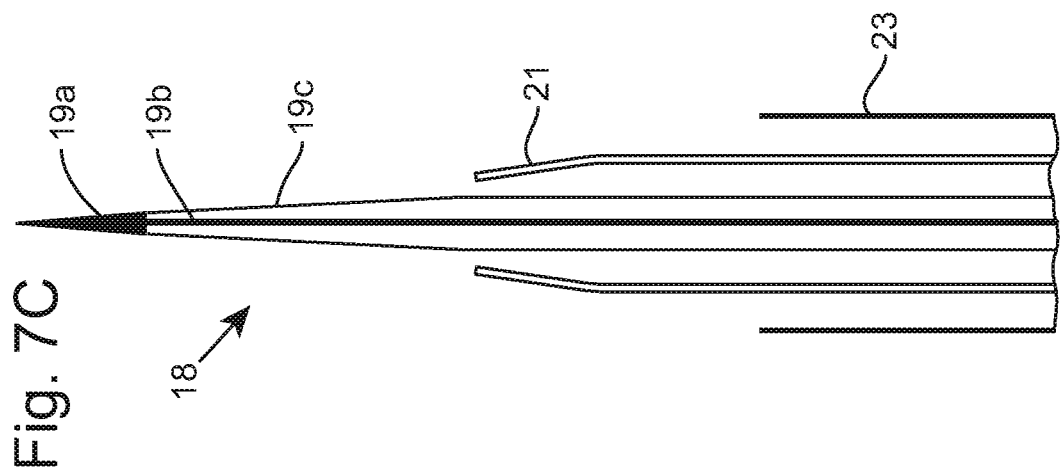
FIGS. 7A to 7C are schematic representations of a percutaneous insertion device according to the present invention.
Figure 7B:
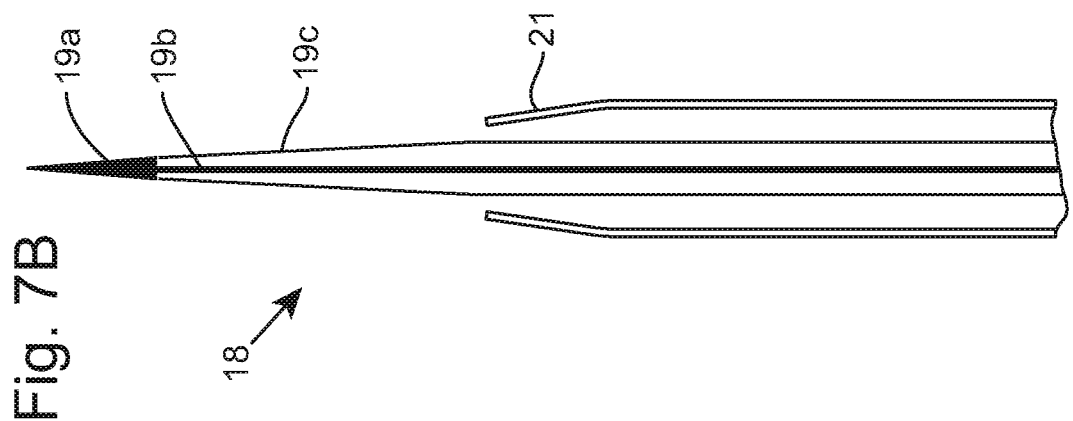
Figure 7A:
Figure 7D:
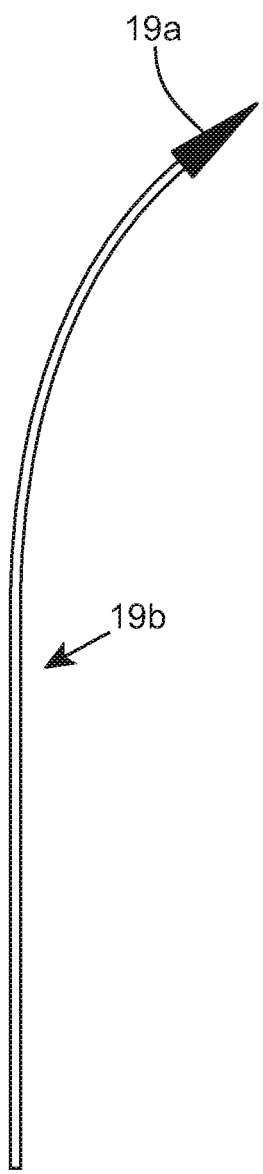
FIGS. 7D' and 7D" are a schematic representation of a percutaneous insertion device according to the present invention in a substantially straight configuration and in a coiled configuration.
Figure 8A:
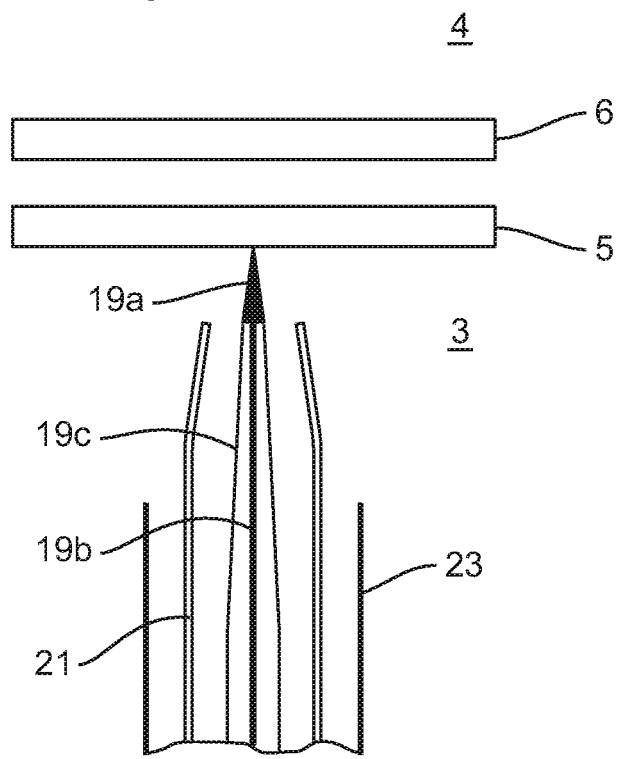
FIGS. 8A to 8J are schematic representations of the puncture, insertion and positioning steps of the methods according to the present invention.
Figure 8B:
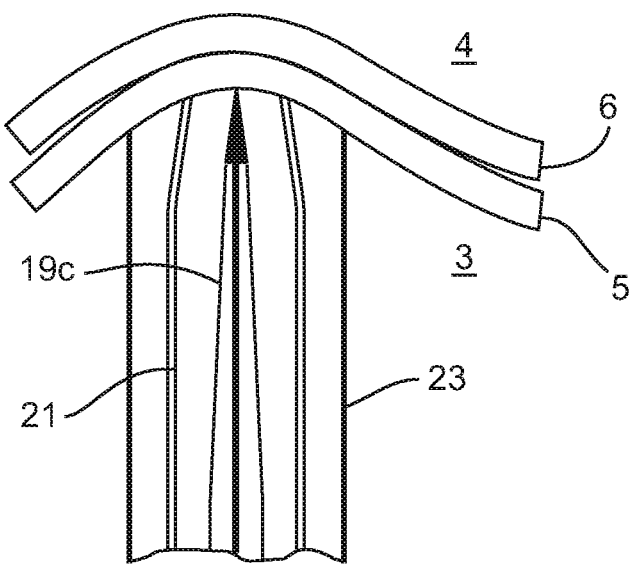
Figure 8C:
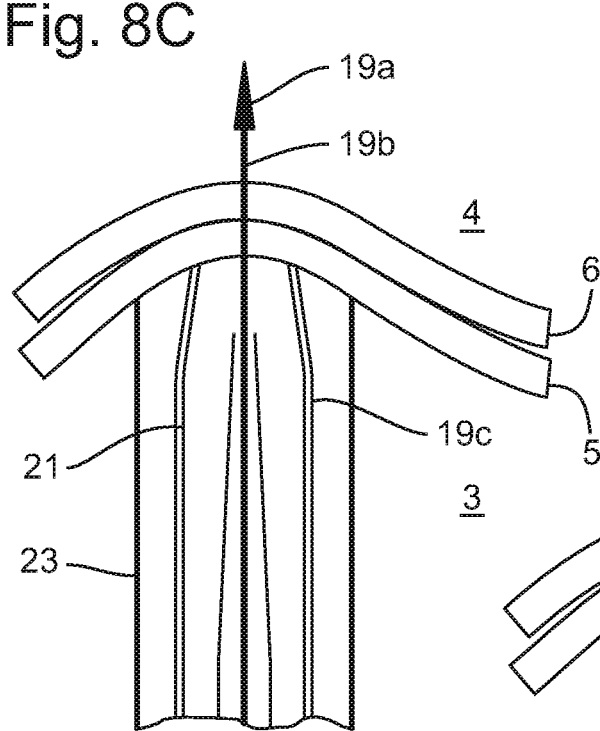
Figure 8D:
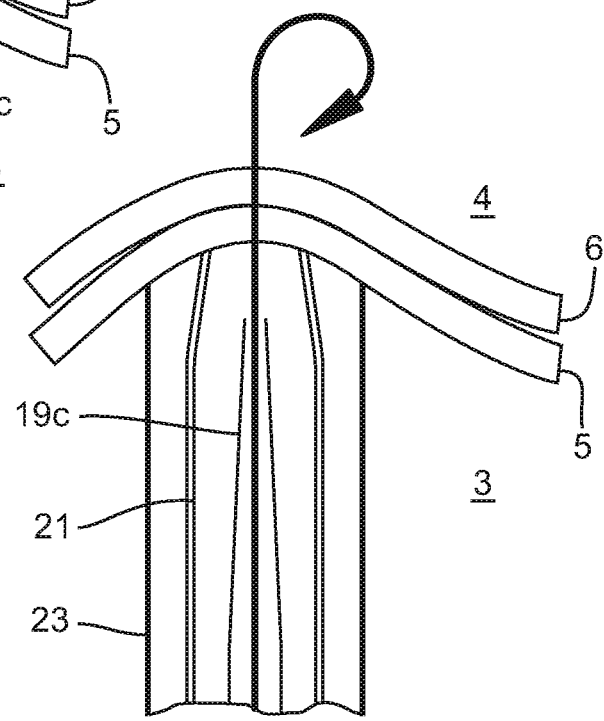
Figure 8E:
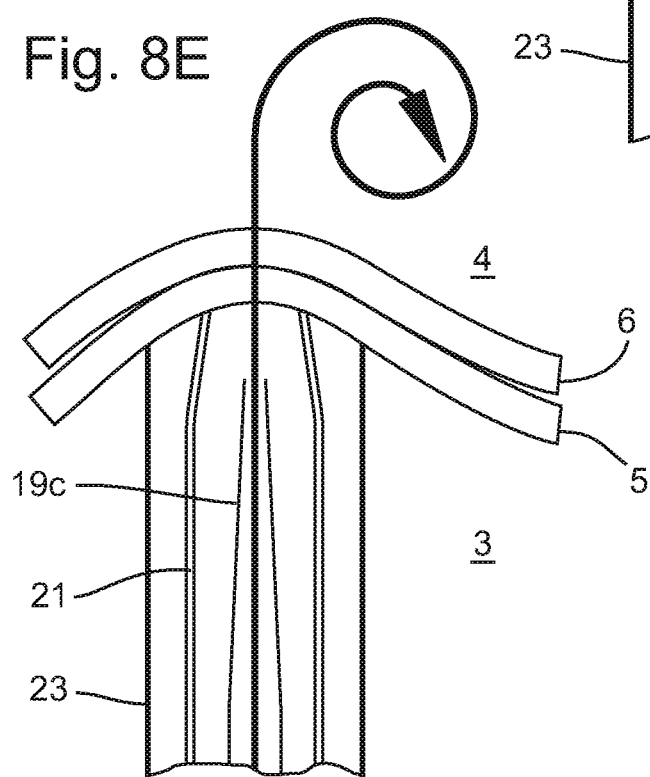
Figure 8F:
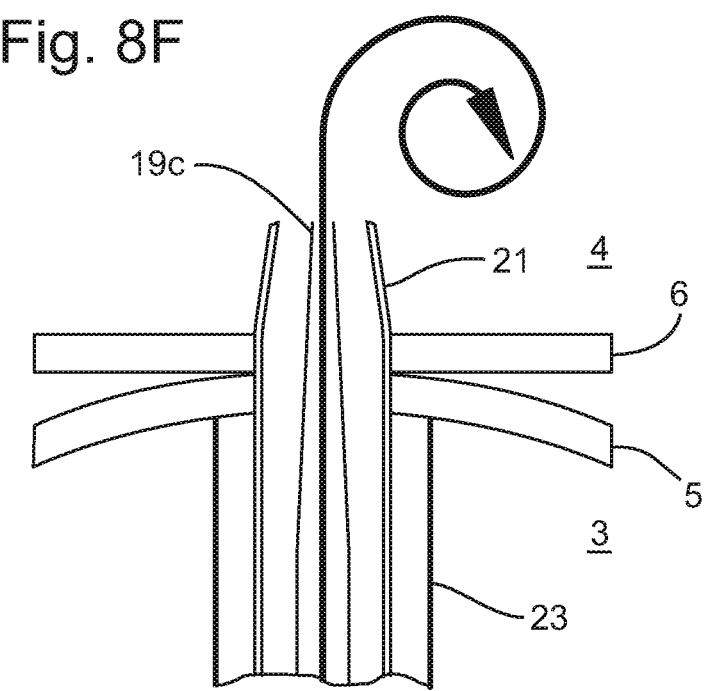
Figure 8G:
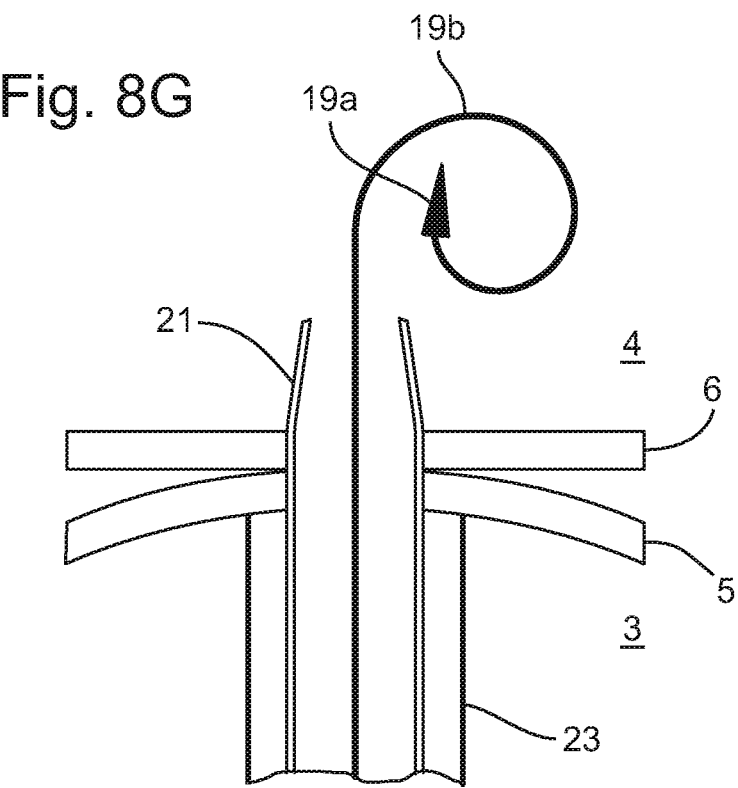
Figure 8H:
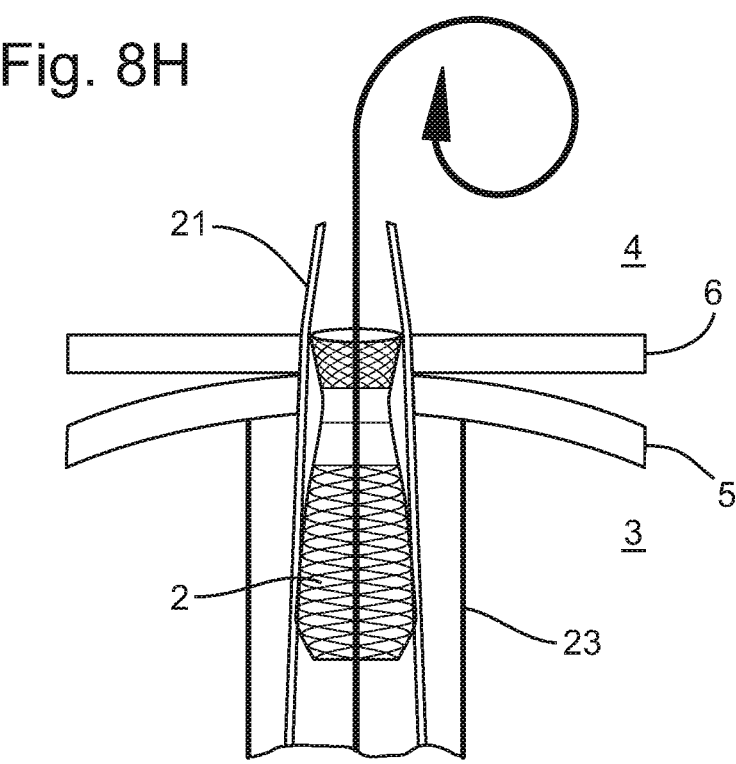
Figure 8I:
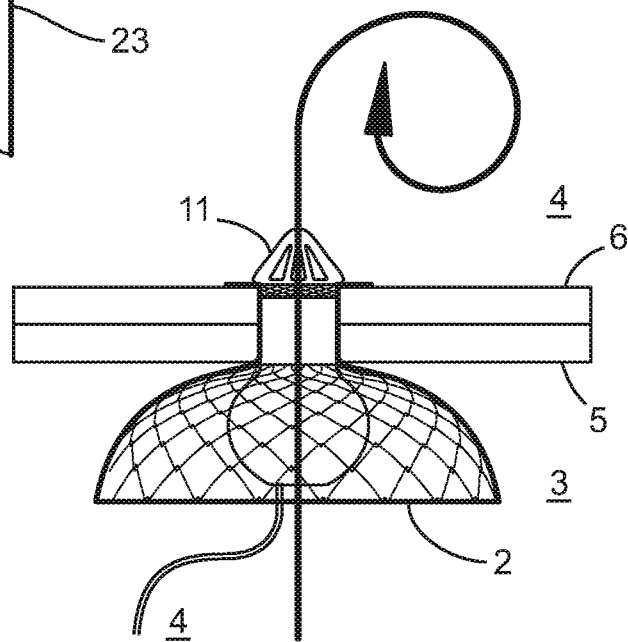
Figure 8J:
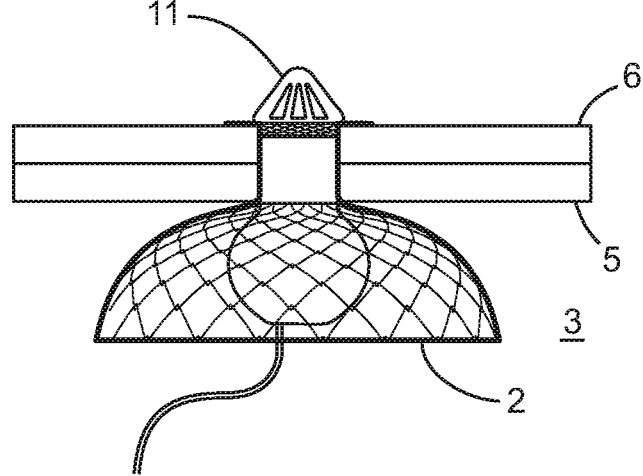

With reference to FIGS. 7D' and 7D", the guide wire 19a comprises at least two sections of different rigidity, namely a proximal portion of relatively rigid material to guide and push the puncture head 19a through the patient's anatomy and a distal portion of more flexible material. The flexible portion is particularly useful to prevent injury to the patient's anatomy for example, when advancing the guide wire 19b or during the step of inserting and position the intracorporeal devices. For example, the flexible portion can coil around the puncture head 19a to protect surrounding tissues and to prevent accidental movement of the puncture head 19a.

As will be described below in more details, the insertion element 18 enables the creation of a safe pathway for the insertion, installation and removal of the various elements of the system 1. More specifically, the insertion device 18 according to the present invention is particularly advantageous for the puncture of an anatomical wall, such as an outer wall of an anatomical compartment which has a greater tissue resistance. The insertions device 18 also enables a particularly accurate and small incision to be created, which is crucial in incisions involving high pressure blood flow. A preferred use of the insertion element 18 is for the puncture of outer walls of internal organs, for example for an extra-cardiac puncture.

A method according to the present invention will now be described by way of example with reference to a left atrium-aorta connection.

Figure 9:
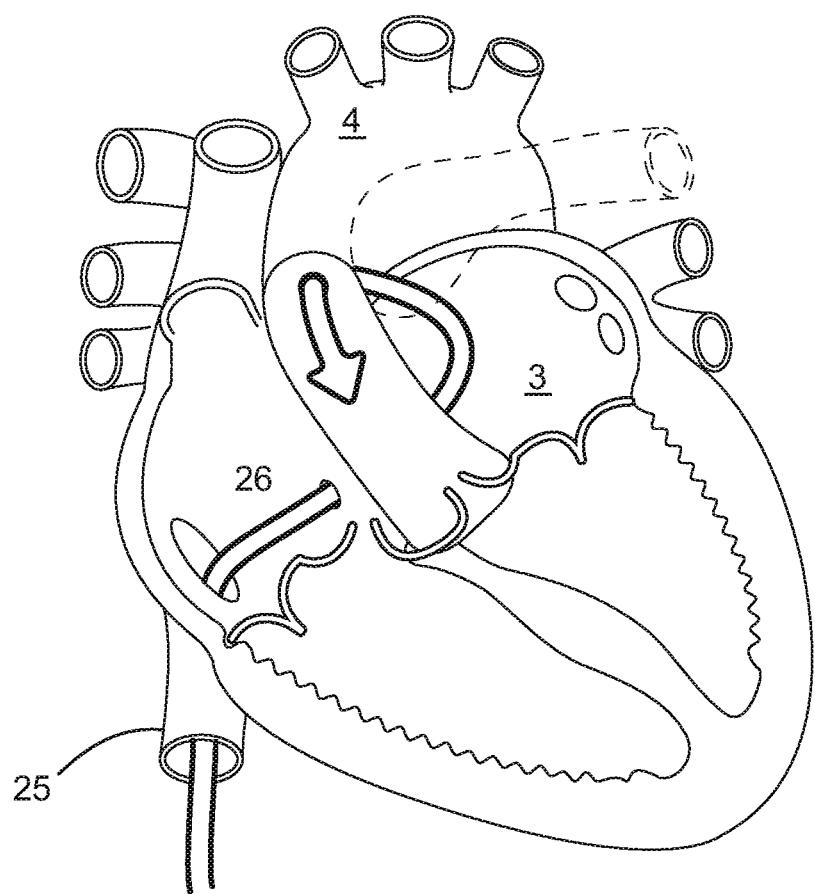
FIG. 9 is an illustration of an insertion route in a method according to the present invention.

The first step is the insertion of a guide wire, which can be carried out by means known in the art. A needle carrying a guide wire is placed on the groin area of the patient, adjacent the femoral artery. Pressure is applied so that the patient's skin is punctured by the tip of the needle and pushed through the skin and tissues into the femoral artery. Once in place, the guide wire is advanced along the femoral artery and up the inferior vena cava 25. With reference to FIG. 9, the guide wire exists the inferior vena cava 25 and enters the right atrium 26. The septal puncture between the right and left atrium can also be carried out by means known in the art. A guide wire now extends from outside the patient, into the femoral artery through the skin puncture, the inferior vena cava 25, the right atrium 26, the atrial septum and the left atrium 3 lodged preferably in superior left pulmonary vein. Next, a large and steerable support sheath can be deployed into the left atrium over the wire to facilitate the final steps of the procedure. The skin puncture and/or septal puncture could equally be carried out using the insertion device 18 according to the present invention, although the insertion device 18 is most advantageous when performing an extra cardiac puncture as described below.

The second step is insertion and installation of the insertion device 18 according to the present invention. The needle 19 is inserted through the groin preferably through dedicated sheaths 21 and 23 and advanced along the same path as described above. The guide wire 19b comprises a relatively flexible (distal) portion adjacent to the puncture head before a more rigid proximal portion, so that as the guide wire 19b folds upon itself at the flexible portion, thereby forming a U-shape. The flexible portion now advances first, followed by the rigid proximal portion. Thus, the guide wire 19b can be moved atraumatically through the delivery sheath or alternatively, through the patient's blood vessels. The guide wire 19b can be straightened when required by gently pulling the proximal end and repositioning the distal portion at its front most position. The puncture head 19a is pulled back towards the distal end of the dilator 19c.

The third step is the extra-cardiac puncture of the left atrium using an insertion device 18 according to the present invention. The distal end of the outer sheath 23 is placed against the roof of the left atrium 3 and pushed against the wall so that the roof of the left atrium 3 contacts the aortic wall. The puncture head is advanced so as to puncture the roof of the left atrium 3. This sharp, conical shape enables the medical professional to create a small and accurate extra-cardiac incision in a smooth and atraumatic manner. The puncture head 19a and dilator 19c are advanced through the puncture towards the aortic wall. The outer sheath 23 is used to push the wall of the left atrium against the aortic wall and hold both walls together to assist puncture of the aortic wall. Once the aortic wall is pierced, the dilator 20 can stretch both punctures to facilitate the insertion of the working sheath 21. The dilator 19c can be removed to leave the guide wire 19b and working sheath 21 in place in the aorta 4. The outer sheath 23 can remain in the left atrium 3.

The puncture head 19a is advanced further into the aorta 4. As it exits the dilator 19c, the flexible portion of the guide wire 19b will coil around the puncture head 19a, thereby anchoring and shielding the puncture head 19a from surrounding tissues. Additionally or alternatively, a receiving catheter may be positioned into the aorta 4 by means known in the art, to receive and protect the puncture head 19a in the aorta.

It can therefore be seen that the support sheath 23 can be used to safely deliver the intracorporeal devices but also assists the puncture of the anatomical wall(s), in particular when the procedure involves the puncture of more than one anatomical wall.

Figure 11:
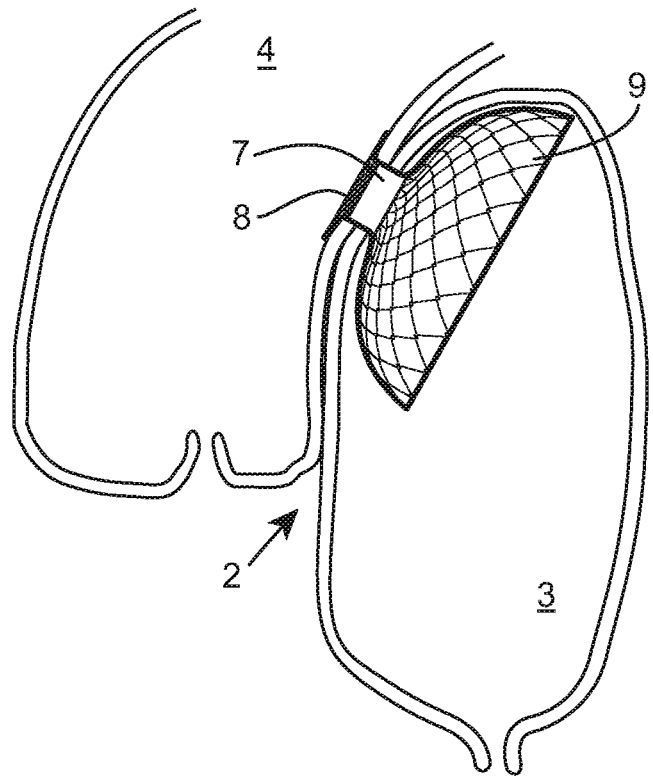
FIG. 11 is a schematic representation of an intracorporeal connector according to the present invention in situ.

The fourth step is the insertion of an intracorporeal connector 2 according to the present invention. With reference to FIGS. 10A and 10B, the intracorporeal connector 2 is inserted in a folded or compressed state into working sheath 21 along the guide wire 19b. When the connector 2 reaches the roof of the left atrium, it is pushed along the guide wire 19b, through the incision in the anatomical walls 5,6 until the neck 7 is correctly positioned across the anatomical walls 5,6 and the anchor 8 and shield 9 are deployed on either side of the walls 5, 6, in the aorta 4 and the left atrium 3, respectively (FIG. 11). The connector 2 gradually expands at it exits the distal end of the working sheath 21.

Figure 4A:
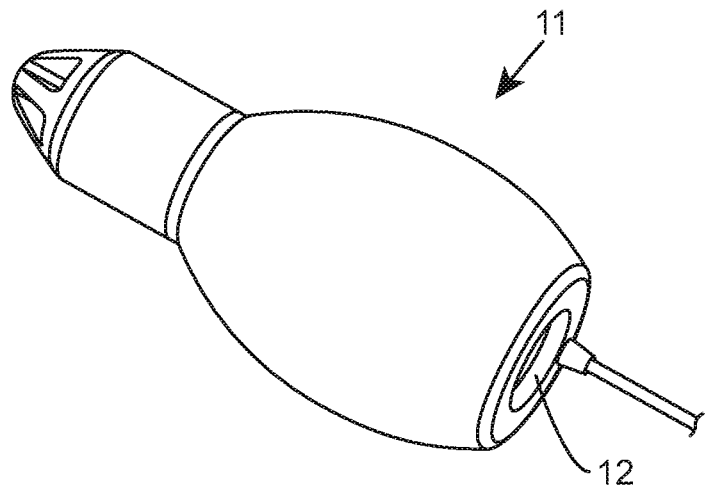
FIGS. 4A and 4B are schematic representations of a flow regulating device according to the present invention.
Figure 4B:
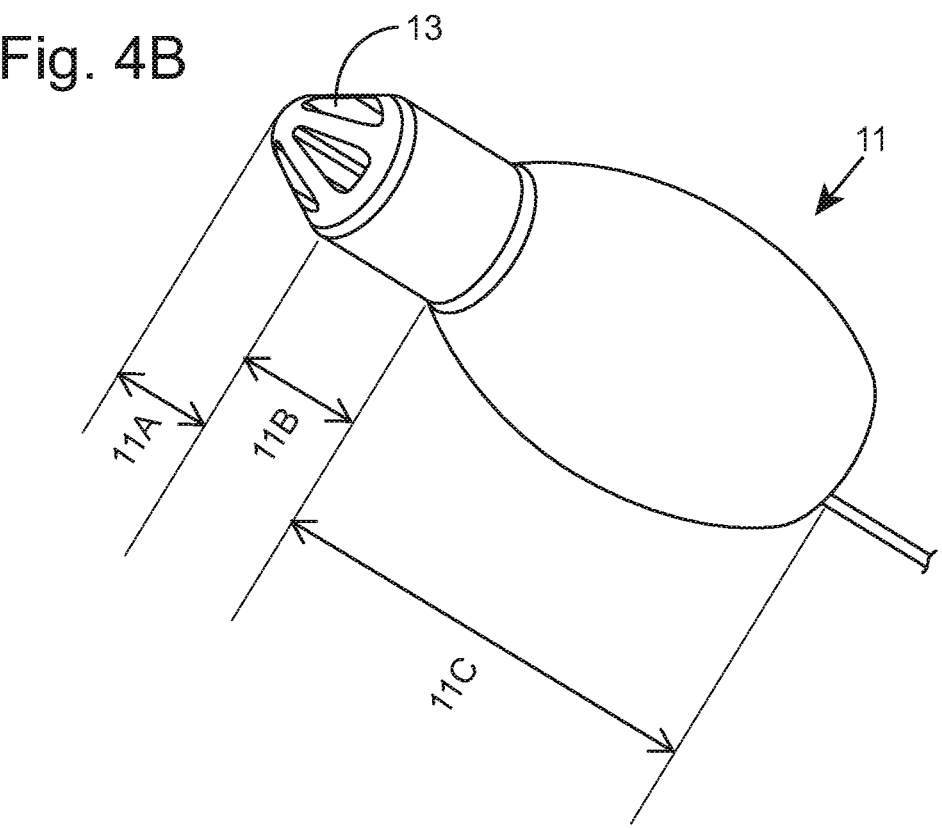
Figure 12:
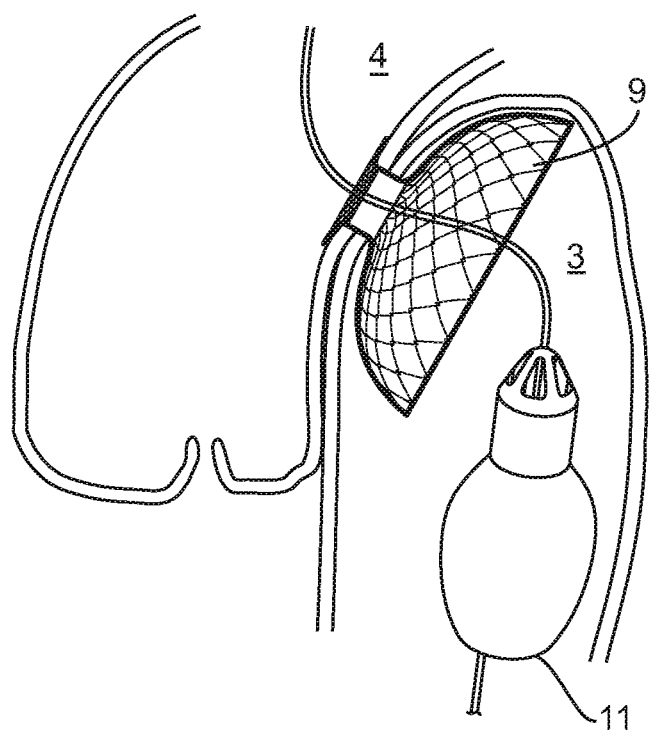
FIG. 12 is an illustration of a flow regulating device according to the present invention during the insertion process.
Figure 13:
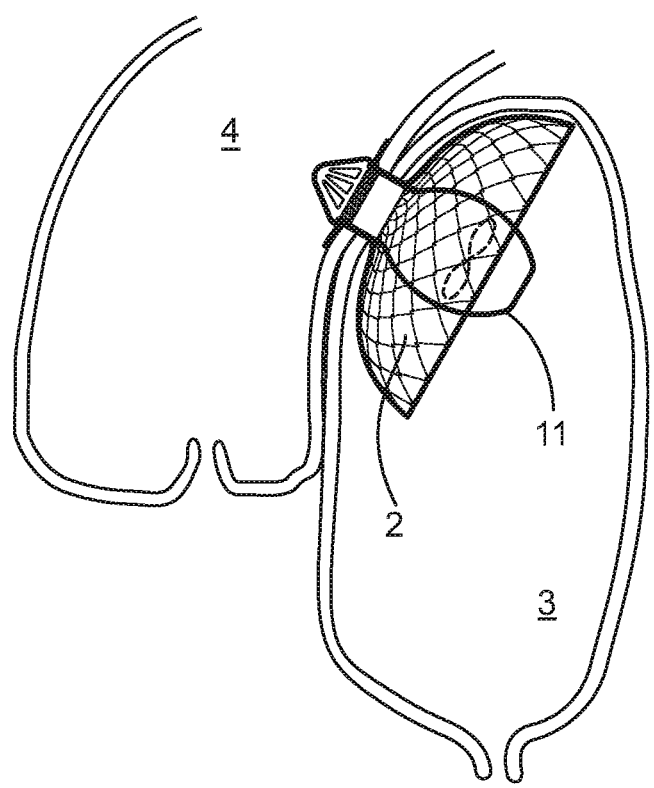
FIG. 13 is a schematic representation of a system according to the present invention in situ.
Figure 14:
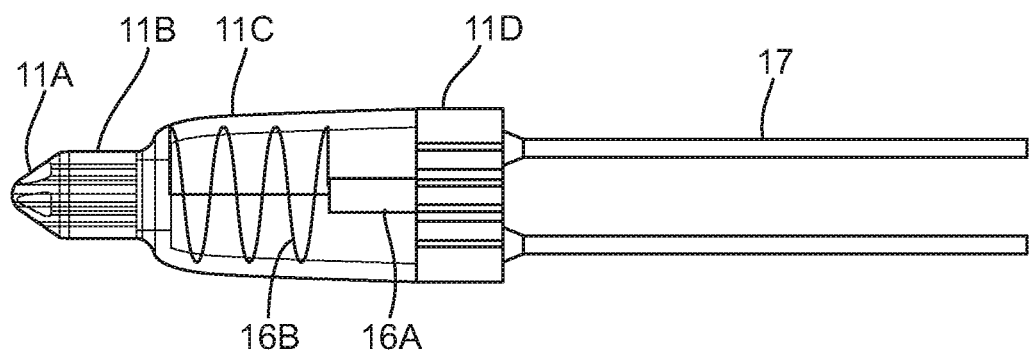
FIGS. 14 and 15 are schematic representations of a first preferred flow regulating device according to the present invention in an inserted state.
Figure 15:
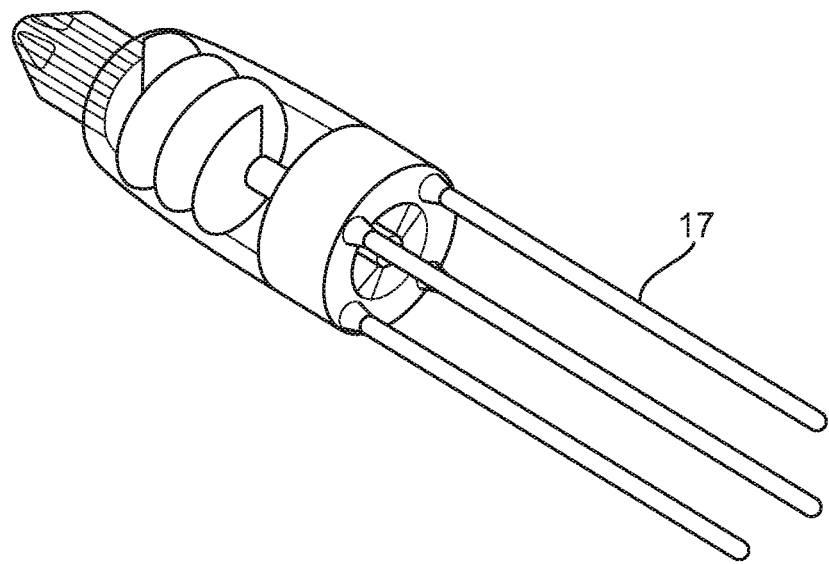

The fifth step is the insertion of an intracorporeal flow regulating device 11 as shown in FIG. 4 or 15 according to the present invention. With reference to FIG. 12, the intracorporeal flow regulating device 11 is inserted and advanced through the sheath 21 and along the guide wire 19b until it reaches the connector 2. The distal portion 11A and more particularly the distal tip of the connector 2 acts as an actuator which opens the gate 10 in the neck 7 of the connector 7 by stretching the opening 10A of the gate 10. The intermediate portion 11B of the flow regulating device 11 sits in the neck 7 of the connector 2 and is securely positioned. The flow regulating device 11 can be secured due to the pressure of the resilient material of the gate 10 and by ribs 14. Additionally or alternatively, the flow regulating device 11 can be secured by screwing the intermediate portion 11B of the flow regulating device 11 to the neck 7 of the connector 2. This screwing mechanism also enables the safe and guided advancement of the flow regulating device 11 into the connector 2. Where provided, sealing means prevent any leakage through the coupling interface between the flow regulating device 11 and the connector 2. Unless further required, the working sheath 21 can now be removed.

It can therefore be seen that the insertion device 18 according to the present invention serves a dual purpose. Firstly, the puncture head 19a can be used in puncturing the anatomical wall(s) in a safe, controlled and atraumatic manner. Secondly, the insertion device 18 can used as an integrated guide wire 19b. There is therefore no need for a needle and a separate guide wire to be used in two separate steps. This minimises the risk of accidents and injuries and simplifies the insertion procedure.

In the case of a compressible/expandable flow regulating device as shown in FIGS. 16 to 19, the base 11D of device 11 is detached from the proximal portion 11C and the blade 16B is stretched to its extended position. For example, the base 11D is rotated or unscrewed so that simultaneously, the base 11D is detached from proximal portion 11C and the blade 16B is extended. The device 11 is advanced to the distal end of the sheath 21 and the distal portion 11A of the device 11 suitably positioned ready to actuate gate 10. The base 11D is re-attached to the proximal portion 11C of the device 11, for example by rotating of screwing, so that the blade 16B relaxes into its working configuration. The distal portion 11A of the flow regulating device 11 can now be pushed through the gate 10 to allow fluid flow.

The insertion and installation procedures described above can be facilitated by visualisation techniques such as X-ray, fluoroscopy, echocardiography, ultrasound techniques.

The pump 16 is started and blood flow between the left atrium 3 and the aorta 4 can be adjusted. The blood flows from the left atrium 3 into the proximal end of the device 11, through the device and exits through the apertures 13 at the distal end of the device 11 into the aorta 4. Blood flow, timing of blood flow, temperature and other parameters can be controlled and adjusted. Similarly, drugs and/or oxygen can be added and/or contaminants removed from the blood as it passes through the device 11. As the blood is sucked into the device 11, surrounding tissues are prevented from hindering the blood passage by the shield 9. The blood flow has a tendency of pushing the device 11 backwards into the left atrium but the device 11 is immobilised by the securing means as described above.

The flow regulating device 11 may be removed from the patient when the treatment is completed, if charging, repair or replacement is required. A sheath 21, 23 is inserted through the patient's anatomy and a dedicated (un)coupling device 35 is used which comprising means for coupling with the flow regulating device 11. The (un)coupling device attaches to the flow regulating device 11 for example by means of one or more engaging tabs 36a engaging into corresponding recesses 36b in the flow regulating device 11. The attachment means is remotely controllable. The (un) coupling device comprises a rotation means for unscrewing the flow regulating device 11 from the connector 2 and the flow regulating device 11 can be safely retrieved through the sheath 21,23. The (un)coupling device may also be used in the insertion process to advance the flow regulating device 11 through the sheaths 21,23 and to screw the flow regulating device 11 to the connector 2.

Upon removing the device 11, the gate 11 closes and blood flow is halted and the connector 2 can remain in place or be removed.

Although the present invention has been described with respect to a left atrium to aorta procedure, the system and method can also be applied to other delivery sites including, but not limited to, right atrium-aorta, vena cava-pulmonary artery, vena cava-aorta. Thus, the present invention can be broadly applied for example as left ventricular assist devices (LVAD), right ventricular assist devices (RVAD) or biventricular assist devices (BiVAD), for cardiopulmonary support (CPS) or for intra-corporeal membrane oxygenation (ICMO) or bubble oxygenation, for the treatment of other organs with pressure issues (e.g. gastric or neurological procedures). The present invention is versatile and a wide variety of applications can therefore be envisaged.

From the above description, it can be seen that the present invention constitutes a novel alternative to existing percutaneous procedures. The present percutaneous procedure requires limited mechanical apparatus and devices and offers a simple as well as safer and cheaper alternative to existing procedures. All the elements are inserted and implanted percutaneously so that there is no need for invasive and traumatic open surgery. Furthermore, the devices described herein can be easily be applied to paediatric treatments.

It is important to note that the present invention relies on an artificially created fluid pathway. Cardiopulmonary or circulatory collapse and heart failure can be the result of a variety of acquired or natural conditions and can affect different anatomical parts of the heart and circulatory and respiratory system. Existing procedures often seek to repair or replace the existing defective anatomical parts. The present invention provides a procedure which is more forgiving in that it relies on artificially created pathways which can by-pass the defective portion of the circulatory system and allow for use of novel treatment principles and technologies compared with current treatments.

It is nonetheless envisaged to use the present invention in cases where the fluid flow through a natural pathway is insufficient, deficient or unregulated and where it becomes necessary to restore a pathway or a fluid flow. This is for example the case with severe pulmonary stenosis, severe aortic stenosis, atresia, and severe MV stenosis.

The present invention allows the safe and atraumatic puncture of structurally sensitive anatomical walls by using an insertion device comprising a guide wire and an integral puncture head as described above. The present invention allows the safe implantation, positioning and working of flow regulating devices using a connector as described above, which preserves the integrity of structurally sensitive walls. The present invention allows the treatment of vulnerable patients who may have anatomical deficiencies which prevent them from being treated with conventional methods. The present invention allows the treatment of smaller patients, such as children, or where it is not possible to use or introduce bulky devices. The present invention provides a minimally invasive procedure which does not compromise the patient's post-procedure mobility.

This system is a safe, stable and predictable structure for the delivery of improved therapeutic instruments from one compartment to another, through shorter and more beneficial routes.

Further aspect of the invention can be found in the following paragraphs.

1. A percutaneous system comprising an intracorporeal connector for fluid communication between two anatomical compartments through at least one anatomical wall.

2. The system according to paragraph 1, wherein the connector comprises a neck for fluid passage from one compartment to the other and means for securing the neck across the anatomical wall.

3. The system according to paragraph 2, wherein the securing means comprises an expandable anchor extending from a first end of the neck.

4. The system according to paragraph 3, wherein, in its expanded state, the anchor lies substantially parallel to the anatomical wall.

5. The system according to any one of paragraphs 2 to 4, wherein the connector comprises means for preventing tissue from hindering fluid passage through the neck.

6. The system according to paragraph 5, wherein the prevention means comprises an expandable shield extending from a second end of the neck.

7. The system according to paragraph 6, wherein the shield in its expanded state does not substantially contact the anatomical wall.

8. The system according to any preceding paragraph, wherein the connector is made wholly or partly of a shape memory material.

9. The system according to any one of paragraphs 2 to 8, wherein the neck comprises a gate to selectively prevent or allow passage of fluid through the neck.

10. The system according to any preceding paragraph, further comprising an intracorporeal device for regulating the flow of fluid between the two anatomical compartments.

11. The system according to paragraph 10, wherein the flow regulating device comprises an actuator to allow or prevent fluid flow through the intracorporeal connector.

12. The system according to paragraphs 11 or 12, wherein the flow regulating device comprises a pump.

13. The system according to any preceding paragraph, further comprising means for treating the fluid.

14. The system according to paragraph 13, wherein the fluid treatment means comprises means for contacting the fluid with one or more drug compounds.

15. The system according to paragraphs 13 or 14, wherein the fluid treatment means comprises means for contacting the fluid with one or more gas, such as oxygen.

16. The system according to any one of paragraphs 10 to 15, further comprising means for securing the flow regulating means to the connector.

17. The system according to any one of paragraphs 10 to 16, wherein the flow regulating means comprises a rotatable shaft supporting at least one blade, said blade being adapted for extension in the longitudinal direction of the shaft into an insertion configuration.

18. The system according to paragraph 17, wherein the blade is adapted for relaxation in the longitudinal direction of the shaft into a working configuration.

19. The system according to paragraph 18, wherein, in the lateral direction of the shaft, the dimension of the blade is greater in the working configuration than in the insertion configuration.

20. The system according to any one of paragraphs 17 to 19, wherein the blade is a screw type blade.

21. The system according to any one of paragraphs 17 to 20, wherein the blade is made of a longitudinally resilient material.

22. The system according to any preceding paragraph, wherein one or both anatomical compartments are compartments of the circulatory system.

23. The system according to any preceding paragraph, wherein the fluid is blood.

24. The system according to any preceding paragraph, wherein the system is a ventricular assist device.

25. The system according to any preceding paragraph, further comprising a percutaneous insertion device comprising a needle, said needle comprising a needle body, a guide wire and a puncture head.

26. The system according to paragraph 25, wherein the puncture head comprises a solid tip.

27. The system according to paragraph 25 or 26, wherein the dimensions of the widest cross section of the puncture head are substantially the same as those of the cross section of the distal end of the guide wire.

28. The system according to any one of paragraphs 25 to 27, wherein the insertion device further comprises a dilator.

29. The system according to paragraph 28, wherein the dimensions of the widest cross section of the puncture head are substantially the same as those of the distal end of the dilator.

30. The system according to any one of paragraphs 25 to 29, wherein the insertion device further comprises means for guiding a sheath.

31. An intracorporeal connector as specified in any preceding paragraph.

32. An intracorporeal flow regulating device as specified in any one of paragraphs 10 to 21.

33. A percutaneous insertion device as specified in any one of paragraphs 25 to 30.

34. A percutaneous method for providing fluid communication between two anatomical compartments, the method comprising the steps of puncturing the wall(s) separating the compartments and
inserting an intracorporeal connector through the puncture(s) for fluid communication between the two compartments.

35. The method according to paragraph 34, wherein the puncturing step is carried out using an insertion device as specified in any one of claims 25 to 30.

36. The method according to paragraph 34 or 35, wherein the intracorporeal connector is a connector as specified in any one of paragraphs 1 to 30.

37. The method according to any one of paragraphs 34 to 36, further comprising the step of regulating the flow of fluid between the two anatomical compartments.

38. The method according to paragraph 37, wherein the flow of fluid is regulated using an intracorporeal flow regulating device as specified in any one of paragraphs 10 to 30.

39. The method according to any one of paragraphs 34 to 38, further comprising the step of treating the fluid.

40. The method according to paragraph 38, wherein the treatment of the fluid is carried out using the treatment means as specified in any one claims 13 to 15.

41. The method according to any one of paragraph 34 to 40 wherein one or both compartments are compartments of the circulatory system.

The invention claimed is:

1. A transcatheter system comprising:
a first device which is an intracorporeal connector for fluid communication between two anatomical compartments through at least one anatomical wall, wherein said connector is adapted to receive a flow regulating device, wherein said connector comprises a neck for fluid passage from one anatomical compartment to another anatomical compartment; and
a second device which is an intracorporeal flow regulating device for regulating the flow of fluid between said two anatomical compartments through said at least one anatomical wall wherein the flow regulating device comprises a pump, wherein the pump comprises a single pump housing, and wherein the single pump housing comprises a rotatable shaft supporting at least one blade located within the single pump housing, and
complementary screwing means for detachably securing the intracorporeal flow regulating device to the intracorporeal connector, the screwing means located on an inner surface of the neck of the intracorporeal connector and an outer surface of an intermediate portion of the intracorporeal flow regulating device such that the intracorporeal flow regulating device is configured to be coupled to the intracorporeal connector when the intracorporeal flow regulating device and the intracorporeal connector are disposed across said at least one anatomical wall.

2. The system according to claim 1, wherein the flow regulating device comprises an actuator to allow or prevent fluid flow through the intracorporeal connector.

3. The system according to claim 1, wherein the flow regulating device comprises a first portion located in use in the first compartment, a second portion located in use in the second compartment, and an intermediate portion located in use through the anatomical wall(s).

4. The system according to claim 3, wherein the first portion and/or the second portion comprises one or more apertures for fluid passage from the first compartment to the second compartment.

5. The system according to claim 3, wherein the first portion comprises a cross-section of larger diameter than the diameter of the cross-section of the intermediate portion.

6. The system according to claim 1, wherein when the flow regulating device is coupled to the connector, fluid can flow from the first compartment to the second compartment, and when the flow regulating device is not coupled to the connector, fluid is prevented from flowing from the first compartment to the second compartment.

7. The system according to claim 1, wherein the pump comprises an inverted screw pump.

8. The system according to claim 1, wherein the flow regulating device is adapted to receive a guide wire therethrough.

9. The system according to claim 1, further comprising means for sealing the complementary screwing means.

10. The system according to claim 1, wherein the connector comprises means for securing the neck across the anatomical wall.

11. The system according to claim 10, wherein the securing means comprises an expandable anchor extending from a first end of the neck.

12. The system according to claim 11, wherein, in its expanded state, the anchor lies substantially parallel to the anatomical wall of the second compartment.

13. The system according to claim 10, wherein the connector comprises means for preventing tissue from hindering fluid passage through the neck.

14. The system according to claim 13, wherein the prevention means comprises an expandable shield extending from a second end of the neck.

15. The system according to claim 1, wherein the connector further comprises a gate to selectively prevent or allow passage of fluid from the first compartment to the second compartment.

16. The system according to claim 15, wherein the gate is capable of allowing passage of fluid when the flow regulating device is received therethrough, and prevents passage of fluid in the absence of the flow regulating device.

17. The system according to claim 1, wherein the connector is collapsible.

* * * * *